(12) United States Patent
Skordalakes

(10) Patent No.: US 8,377,992 B2
(45) Date of Patent: Feb. 19, 2013

(54) TRBD-BINDING EFFECTORS AND METHODS FOR USING THE SAME TO MODULATE TELOMERASE ACTIVITY

(75) Inventor: Emmanuel Skordalakes, Philadelphia, PA (US)

(73) Assignee: The Wistar Institute, Philadelphia, PA (US)

( * ) Notice: Subject to any disclaimer, the term of this patent is extended or adjusted under 35 U.S.C. 154(b) by 209 days.

(21) Appl. No.: 12/701,843

(22) Filed: Feb. 8, 2010

(65) Prior Publication Data

US 2010/0160260 A1    Jun. 24, 2010

Related U.S. Application Data

(63) Continuation-in-part of application No. PCT/US2008/080604, filed on Oct. 21, 2008.

(60) Provisional application No. 61/090,726, filed on Aug. 21, 2008, provisional application No. 60/981,548, filed on Oct. 22, 2007.

(51) Int. Cl.
    *A61K 31/135*    (2006.01)
(52) U.S. Cl. ...................................... 514/657
(58) Field of Classification Search .................. 514/657
    See application file for complete search history.

(56) References Cited

U.S. PATENT DOCUMENTS

| | | | |
|---|---|---|---|
| 5,645,986 A | 7/1997 | West et al. | 435/6 |
| 5,804,380 A | 9/1998 | Harley et al. | 435/6 |
| 5,856,096 A | 1/1999 | Windle et al. | 435/6 |
| 6,342,358 B1 | 1/2002 | Collins et al. | 435/6 |
| 6,358,687 B1 | 3/2002 | Chabot et al. | 435/6 |
| 6,368,789 B1 | 4/2002 | West et al. | 435/6.18 |
| 6,517,834 B1 | 2/2003 | Weinrich et al. | 424/94.5 |
| 6,623,930 B2 | 9/2003 | Kerwin et al. | 435/6 |
| 6,638,789 B1 | 10/2003 | Glenn et al. | 438/109 |
| 6,787,133 B2 | 9/2004 | Weinrich et al. | 424/94.5 |
| 6,906,237 B2 | 6/2005 | Herron | 800/8 |
| 7,067,283 B2 | 6/2006 | Weinrich et al. | 435/69.2 |
| 2006/0040307 A1 | 2/2006 | Cech et al. | 435/6 |

OTHER PUBLICATIONS

CAS Registry—STN Substance Record for 402591-62-2, Entered STN Mar. 22, 2002.*
Autexier, C. and Lue, N.F. "The Structure and Function of Telomerase Reverse Transcriptase" Annual Review of Biochemistry 2006 vol. 75: 493-517.
Lee et al. "Human Telomerase Reverse Transcriptase Motifs Required for Elongation of a Telomeric Substrate" The Journal of Biological Chemistry 2003 vol. 278(52): 52531-52536.
Peng et al. "Analysis of Telomerase Processivity: Mechanistic Similarity to HIV-1 Reverse Transcriptase and Role in Telomere Maintenance" Molecular Cell 2001 vol. 7: 1201-1211.
Collins, K. and Ghandi, L. "The Reverse Transcriptase Component of the *Tetrahymena* Telomerase Ribonucleoprotein Complex" Proceedings of the National Academy of Science USA 1998 vol. 95: 8485-8490.
Bryan et al. "Telomerase Reverse Transcriptase Genes Identified in *Tetrahymena thermophila* and *Oxytricha trifallax*" Proceedings of the National Academy of Science USA 1998 vol. 95: 8479-8484.
Jacobs et al. "Soluble Domains of Telomerase Reverse Transcriptase Indentified by High-Throughput Screening" Protein Science 2005 vol. 14: 2051-2058.
Friedman, K.L. and Cech, T.R. "Essential Functions of Amino-Terminal Domains in the Yeast Telomerase Catalytic Subunit Revealed By Selection for Viable Mutants" Genes & Development 1999 vol. 13: 2863-2874.
Friedman et al. "N-Terminal Domain of Yeast Telomerase Reverse Transcriptase: Recruitment of Est3p to the Telomerase Complex" Molecular Biology of the Cell 2003 vol. 14: 1-13.
Hammond et al. "The Anchor Site of Telomerase from *Euplotes aediculatus* Revealed by Photo-Cross-Linking to Single- and Double-Stranded DNA Primers" Molecular and Cellular Biology 1997 vol. 17(1): 296-308.
Jacobs et al. "Crystal Structure of the Essential N-Terminal Domain of Telomerase Reverse Transcriptase" Nature Structural and Molecular Biology 2006 vol. 13(3): 218-225.
Wyatt et al. "Characterization of Physical and Functional Anchor Site Interactions in Human Telomerase" Molecular & Cellular Biology 2007 vol. 27(8): 3226-3240.
Lai et al. "RNA Binding Domain of Telomerase Reverse Transcriptase" Molecular and Cellular Biology 2001 vol. 21(4): 990-1000.
Bryan et al. "Telomerase RNA Bound by Protein Motifs Specific to Telomerase Reverse Transcriptase" Molecular Cell 2000 vol. 6: 493-499.
Cunningham, D.D. and Collins, K. "Biological and Biochemical Functions of RNA in the *Tetrahymena* Telomerase Holoenzyme" Molecular and Cellular Biology 2005 vol. 25(11): 4442-4454.
Lai et al. "Template Boundary Definition in *Tetrahymena* Telomerase" Genes & Development 2002 vol. 16: 415-420.
Miller, M.C. and Collins, K. "Telomerase Recognizes its Template by Using an Adjacent RNA Motif" Proceedings of the National Academy of Science USA 2002 vol. 99(10): 6585-6590.
O'Connor et al. "Two Purified Domains of Telomerase Reverse Transcriptase Reconstitute Sequence-Specific Interactions with RNA" The Journal of Biological Chemistry 2005 vol. 280(17): 17533-17539.
Lai et al. "Roles for RNA in Telomerase Nucleotide and Repeat Addition Processivity" Molecular Cell 2003 vol. 11: 1673-1683.
Greider, C.W. and Blackburn, E.H. "A Telomeric Sequence in the RNA of *Tetrahymena* Telomerase Required for Telomere Repeat Synthesis" Nature 1989 vol. 337: 331-337.
Zappulla, D.C. and Cech, T.R. "Yeast Telomerase RNA: A Flexible Scaffold for Protein Subunits" Proceedings of the National Academy of Science USA 2004 vol. 101(27): 10024-10029.
Chen et al. "Secondary Structure of Vertebrate Telomerase RNA" Cell 2000 vol. 100: 503-514.
Ly et al. "Comprehensive Structure-Function Analysis of the Core Domain of Human Telomerase RNA" Molecular and Cellular Biology 2003 vol. 23(19): 6849-6856.

(Continued)

Primary Examiner — Barbara P Badio
Assistant Examiner — Sara E Townsley
(74) Attorney, Agent, or Firm — Licata & Tyrrell P.C.

(57) ABSTRACT

The present invention embraces compounds selected for interacting with the T-pocket of telomerase and use thereof for modulating the activity of telomerase and preventing or treating diseases or conditions associated with telomerase.

1 Claim, 4 Drawing Sheets

OTHER PUBLICATIONS

Chen, J. and Greider, C.W. "Template Boundary Definition in Mammalian Telomerase" Genes & Development 2003 vol. 17: 2747-2752.
Chen, J. and Greider, C.W. "Telomerase RNA Structure and Function: Implications for Dyskeratosis Congenita" Trends in Biochemical Sciences 2004 vol. 29(4): 183-192.
Theimer, C.A. and Feigon, J. "Structure and Function of Telomerase RNA" Current Opinion in Structural Biology 2006 vol. 16 : 307-318.
Licht, J.D. and Collins, K. "Telomerase RNA Function in Recombinant *Tetrahymena* Telomerase" Genes & Development 1999 vol. 13: 1116-1125.
Aisner et al. "Telomerase Regulation: Not Just Flipping the Switch" Current Opinion in Genetics & Development 2002 vol. 12: 80-85.
Cong et al. "Human Telomerase and Its Regulation" Microbiology and Molecular Biology Reviews 2002 vol. 66(3): 407-425.
Dong et al. "Telomerase: Regulation, Function and Transformation" Critical Reviews in Oncology/Hematology 2005 vol. 54: 85-93.
Loayza, D. and de Lange, T. "Telomerase Regulation at the Telomere: A Binary Switch" Cell 2004 vol. 117: 279-280.
Smogorzewska, A. and de Lange, T. "Regulation of Telomerase by Telomeric Proteins" Annual Review of Biochemistry 2004 vol. 73: 177-208.
Smogorzewska et al. "Control of Human Telomere Length by TRF1 and TRF2" Molecular and Cellular Biology 2000 vol. 20(5): 1659-1668.
Witkin, K.L. and Collins, K. "Holoenzyme Proteins Required for the Physiological Assembly and Activity of Telomerase" Genes & Development 2004 vol. 18: 1107-1118.
Witkin et al. "Positive and Negative Regulation of *Tetrahymena* Telomerase Holoenzyme" Molecular and Cellular Biology 2007 vol. 27(6): 2074-2083.
Aigner, S. and Cech, T.R. "The *Euplotes* Telomerase Subunit p43 Stimulates Enzymatic Activity and Processivity in Vitro" RNA 2004 vol. 10(7): 1108-1118.
Aigner et al. "The *Euplotes* La Motif Protein p43 Has Properties of a Telomerase-Specific Subunit" Biochemistry 2003 vol. 42(19): 5736-5747.
O'Connor, C.M. and Collins, K. "A Novel RNA Binding Domain in *Tetrahymena* Telomerase p65 Initiates Hierarchical Assembly of Telomerase Holoenzyme" Molecular and Cellular Biology 2006 vol. 26(6): 2029-2036.
Prathapam et al. "A Telomerase Holoenzyme Protein Enhances Telomerase RNA Assembly with Telomerase Reverse Transcriptase" Nature Structural & Molecular Biology 2005 vol. 12(3): 252-257.
Evans, S.K. and Lundblad, V. "The Est1 Subunit of *Saccharomyces cerevisiae* Telomerase Makes Multiple Contributions to Telomere Length Maintenance" Genetics 2002 vol. 162: 1101-1115.
Hughes et al. "The Role of the *EST* Genes in Yeast Telomere Replication" Ciba Foundation Symposium 1997 vol. 211: 41-52.
Lundblad, V. "Telomere Replication: An Est Fest" Current Biology 2003 vol. 13: R439-R441.
Lundblad, V. and Blackburn, E.H. "RNA-Dependent Polymerase Motifs in EST1: Tentative Identification of a Protein Component of an Essential Yeast Telomerase" Cell 1990 vol. 60: 529-530.
Reichenbach et al. "A Human Homolog of Yeast Est1 Associates with Telomerase and Uncaps Chromosome Ends When Overexpressed" Current Biology 2003 vol. 13: 568-574.
Snow et al. "Functional Conservation of the Telomerase Protein Est1p in Humans" Current Biology 2003 vol. 13: 698-704.
Chandra et al. "Cdc13 Both Positively and Negatively Regulates Telomere Replication" Genes & Development 2001 vol. 15: 404-414.
Evans, S.K. and Lundblad, V. "Est1 and Cdc13 as Comediators of Telomerase Access" Science 1999 vol. 286: 117-120.
Lustig, A.J. "Cdc13 Subcomplexes Regulate Multiple Telomere Functions" Nature Structural Biology 2001 vol. 8(4): 297-299.
Pennock et al. "Cdc13 Delivers Separate Complexes to the Telomere for End Protection and Replication" Cell 2001 vol. 104: 387-396.
Bosoy et al. "Conserved N-Terminal Motifs of Telomerase Reverse Transcriptase Required for Ribonucleoprotein Assembly in Vivo" The Journal of Biological Chemistry 2003 vol. 278(6): 3882-3890.
Xia et al. "Identification of Functionally Important Domains in the N-Terminal Region of Telomerase Reverse Transcriptase" Molecular and Cellular Biology 2000 vol. 20(14): 5196-5207.
Bosoy, D. and Lue, N.F. "Functional Analysis of Conserved Residues in the Putative 'Finger' Domain of Telomerase Reverse Transcriptase" The Journal of Biological Chemistry 2001 vol. 276(49): 46305-46312.
Haering et al. "Analysis of Telomerase Catalytic Subunit Mutants in Vivo and in Vitro in *Schizosaccharomyces pombe*" Proceedings of the National Academy of Science USA 2000 vol. 97(12): 6367-6372.
Hossain et al. "Function Analysis of the C-Terminal Extension of Telomerase Reverse Transcriptase" The Journal of Biological Chemistry 2002 vol. 277(39): 36174-36180.
Lue et al. "A Conserved Telomerase Motif within the Catalytic Domain of Telomerase Reverse Transcriptase Is Specifically Required for Repeat Addition Processivity" Molecular and Cellular Biology 2003 vol. 23(23): 8440-8449.

\* cited by examiner

TRBD-BINDING EFFECTORS AND METHODS FOR USING THE SAME TO MODULATE TELOMERASE ACTIVITY

This application is a continuation-in-part of PCT/US2008/080604, filed Oct. 21, 2008, which claims benefit of priority to U.S. Provisional Patent Application Ser. No. 61/090,726, filed Aug. 21, 2008, and Ser. No. 60/981,548, filed Oct. 22, 2007, the contents of which are incorporated herein by reference in their entireties.

BACKGROUND OF THE INVENTION

Any organism with linear chromosomes faces a substantial obstacle in maintaining the terminal sequence of its DNA often referred to as the "end replication problem" (Blackburn (1984) *Annu. Rev. Biochem.* 53:163-194; Cavalier-Smith (1974) *Nature* 250:467-470; Cech & Lingner (1997) *Ciba Found. Symp.* 211:20-34; Lingner, et al. (1995) *Science* 269: 1533-1534; Lundblad (1997) *Nat. Med.* 3:1198-1199; Ohki, et al. (2001) *Mol. Cell. Biol.* 21:5753-5766). Eukaryotic cells overcome this problem through the use of a specialized DNA polymerase, called telomerase. Telomerase adds tandem, G-rich, DNA repeats (telomeres) to the 3'-end of linear chromosomes that serve to protect chromosomes from loss of genetic information, chromosome end-to-end fusion, genomic instability and senescence (Autexier & Lue (2006) *Annu. Rev. Biochem.* 75:493-517; Blackburn & Gall (1978) *J. Mol. Biol.* 120:33-53; Chatziantoniou (2001) *Pathol. Oncol. Res.* 7:161-170; Collins (1996) *Curr. Opin. Cell Biol.* 8:374-380; Dong, et al. (2005) *Crit. Rev. Oncol. Hematol.* 54:85-93).

The core telomerase holoenzyme is an RNA-dependent DNA polymerase (TERT) paired with an RNA molecule (TER) that serves as a template for the addition of telomeric sequences (Blackburn (2000) *Nat. Struct. Biol.* 7:847-850; Lamond (1989) *Trends Biochem. Sci.* 14:202-204; Miller & Collins (2002) *Proc. Natl. Acad. Sci. USA* 99:6585-6590; Miller, et al. (2000) *EMBO J.* 19:4412-4422; Shippen-Lentz & Blackburn (1990) *Science* 247:546-552). TERT is composed of four functional domains one of which shares similarities with the HIV reverse transcriptase (RT) in that it contains key signature motifs that are hallmarks of this family of proteins (Autexier & Lue (2006) supra; Bryan, et al. (1998) *Proc. Natl. Acad. Sci. USA* 95:8479-8484; Lee, et al. (2003) *J. Biol. Chem.* 278:52531-52536; Peng, et al. (2001) *Mol. Cell.* 7:1201-1211). The RT domain, which contains the active site of telomerase is thought to be involved in loose associations with the RNA template (Collins & Gandhi (1998) *Proc. Natl. Acad. Sci. USA* 95:8485-8490; Jacobs, et al. (2005) *Protein Sci.* 14:2051-2058). TERT however is unique, when compared to other reverse transcriptases in that it contains two domains N-terminal to the RT domain that are essential for function. These include the far N-terminal domain (TEN), which is the least conserved among phylogenetic groups, but is required for appropriate human, yeast and ciliated protozoa telomerase activity in vitro and telomere maintenance in vivo (Friedman & Cech (1999) *Genes Dev.* 13:2863-2874; Friedman, et al. (2003) *Mol. Biol. Cell* 14:1-13). The TEN domain has both DNA- and RNA-binding properties. DNA-binding facilitates loading of telomerase to the chromosomes while RNA-binding is non-specific and the role of this interaction is unclear (Hammond, et al. (1997) *Mol. Cell. Biol.* 17:296-308; Jacobs, et al. (2006) *Nat. Struct. Mol. Biol.* 13:218-225; Wyatt, et al. (2007) *Mol. Cell. Biol.* 27:3226-3240). A third domain, the telomerase RNA binding domain (TRBD), is located between the TEN and RT domains, and unlike the TEN-domain is highly conserved among phylogenetic groups and is essential for telomerase function both in vitro and in vivo (Lai, et al. (2001) *Mol. Cell. Biol.* 21:990-1000). The TRBD contains key signature motifs (CP- and T-motifs) implicated in RNA recognition and binding and makes extensive contacts with stem I and the TBE of TER, both of which are located upstream of the template (Bryan, et al. (2000) *Mol. Cell.* 6:493-499; Cunningham & Collins (2005) *Mol. Cell. Biol.* 25:4442-4454; Lai, et al. (2002) *Genes Dev.* 16:415-420; Lai, et al. (2001) supra; Miller, et al. (2000) supra; O'Connor, et al. (2005) *J. Biol. Chem.* 280:17533-17539). The TRBD-TER interaction is required for the proper assembly and enzymatic activity of the holoenzyme both in vitro and in vivo, and is thought to play an important role (although indirect) in the faithful addition of multiple, identical telomeric repeats at the ends of chromosomes (Lai, et al. (2002) supra; Lai, et al. (2003) *Mol. Cell.* 11:1673-1683; Lai, et al. (2001) supra).

Unlike TERT, TER varies considerably in size between species. For example, in *Tetrahymena thermophila* TER is only 159 nucleotides long (Greider & Blackburn (1989) *Nature* 337:331-337), while yeast harbors an unusually long TER of 1167 nucleotides (Zappulla & Cech (2004) *Proc. Natl. Acad. Sci. USA* 101:0024-10029). Despite the large differences in size and structure, the core structural elements of TER are conserved among phylogenetic groups, suggesting a common mechanism of telomere replication among organisms (Chen, et al. (2000) *Cell* 100:503-514; Chen & Greider (2003) *Genes Dev.* 17:2747-2752; Chen & Greider (2004) *Trends Biochem. Sci.* 29:183-192; Ly, et al. (2003) *Mol. Cell. Biol.* 23:6849-6856; Theimer & Feigon (2006) *Curr. Opin. Struct. Biol.* 16:307-318). These include the template, which associates loosely with the RT domain, and provides the code for telomere synthesis, and the TBE, which partly regulates telomerase's repeat addition processivity. In *Tetrahymena thermophila*, the TBE is formed by stem II and the flanking single stranded regions, and is located upstream and in close proximity to the template (Lai, et al. (2002) supra; Lai, et al. (2003) supra; Licht & Collins (1999) *Genes Dev.* 13:1116-1125). Low-affinity TERT-binding sites are also found in helix IV and the template recognition element (TRE) of *Tetrahymena thermophila* TER.

TERT function is regulated by a number of proteins, some of which act by direct association with the TERT/TER complex, while others act by regulating access of telomerase to the chromosome end through their association with the telomeric DNA (Aisner, et al. (2002) *Curr. Opin. Genet. Dev.* 12:80-85; Cong, et al. (2002) *Microbiol. Mol. Biol. Rev.* 66:407-425; Dong, et al. (2005) supra; Loayza & de Lange (2004) *Cell* 117:279-280; Smogorzewska & de Lange (2004) *Annu. Rev. Biochem.* 73:177-208; Smogorzewska, et al. (2000) *Mol. Cell. Biol.* 20:1659-1668; Witkin & Collins (2004) *Genes Dev.* 18:1107-1118; Witkin, et al. (2007) *Mol. Cell. Biol.* 27:2074-2083). For example, p65 in the ciliated protozoan *Tetrahymena thermophila* or its homologue p43 in *Euplotes aediculatus*, are integral components of the telomerase holoenzyme (Aigner & Cech (2004) *RNA* 10:1108-1118; Aigner, et al. (2003) *Biochemistry* 42:5736-5747; O'Connor & Collins (2006) *Mol. Cell. Biol.* 26:2029-2036; Prathapam, et al. (2005) *Nat. Struct. Mol. Biol.* 12:252-257; Witkin & Collins (2004) supra; Witkin, et al. (2007) supra). Both p65 and p43 are thought to bind and fold TER, a process required for the proper assembly and full activity of the holoenzyme. In yeast, recruitment and subsequent up regulation of telomerase activity requires the telomerase-associated protein Est1 (Evans & Lundblad (2002) *Genetics* 162:1101-1115; Hughes, et al. (1997) *Ciba Found. Symp.* 211:41-52;

Lundblad (2003) *Curr. Biol.* 13:R439-441; Lundblad & Blackburn (1990) *Cell* 60:529-530; Reichenbach, et al. (2003) *Curr. Biol.* 13:568-574; Snow, et al. (2003) *Curr. Biol.* 13:698-704). Est1 binds the RNA component of telomerase, an interaction that facilitates recruitment of the holoenzyme to the eukaryotic chromosome ends via its interaction with the telomere binding protein Cdc13 (Chandra, et al. (2001) *Genes Dev.* 15:404-414; Evans & Lundblad (1999) *Science* 286:117-120; Lustig (2001) *Nat. Struct. Biol.* 8:297-299; Pennock, et al. (2001) *Cell* 104:387-396).

How telomerase and associated regulatory factors physically interact and function with each other to maintain appropriate telomere length is under investigation. Structural and biochemical characterization of these factors, both in isolation and complexed with one another, can be used to determine how the interaction of the TRBD domain with stem I and the TBE of TER facilitate the proper assembly and promote the repeat addition processivity of the holenzyme.

While in vitro and in vivo screening assays have been developed to identify agents which modulate telomerase activity or telomere binding, focus has not been placed on identifying agents with a degree of specificity for particular domains or substrate pockets. See, U.S. Pat. Nos. 7,067,283; 6,906,237; 6,787,133; 6,623,930; 6,517,834; 6,368,789; 6,358,687; 6,342,358; 5,856,096; 5,804,380; and 5,645,986 and US 2006/0040307.

SUMMARY OF THE INVENTION

The present invention features a compound selected for interacting with motifs T, 1 and 2 of the T-pocket of telomerase. In one embodiment, the compound is selected from the group of compounds listed in Table 1. A pharmaceutical composition and methods for using the compound to inhibit or stimulate telomerase activity, and in the prevention or treatment of a disease or disorder associated with telomerase are also provided.

BRIEF DESCRIPTION OF THE DRAWINGS

FIG. 1 shows the structure of telomerase (TERT).

DETAILED DESCRIPTION OF THE INVENTION

Figure 1A:
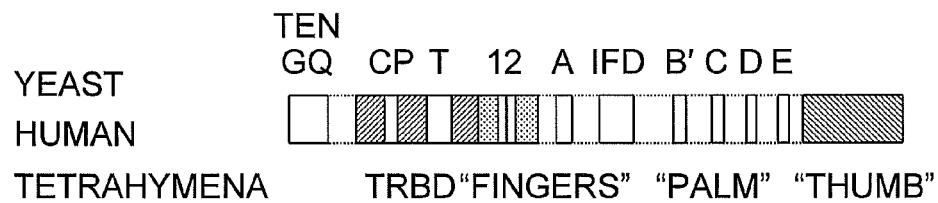
FIG. 1A shows the primary of human, yeast and *Tetrahymena thermophila* TERT showing the functional domains and conserved motifs.
Figure 1B:
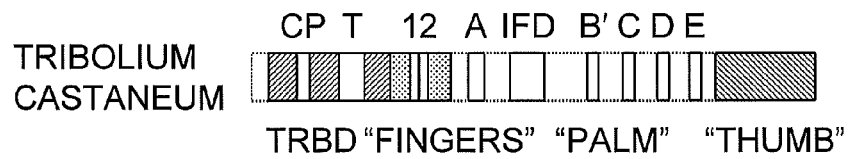
FIG. 1B is the primary structure and conserved motifs of the *Tribolium castaneum* TERT.
Figure 1C:
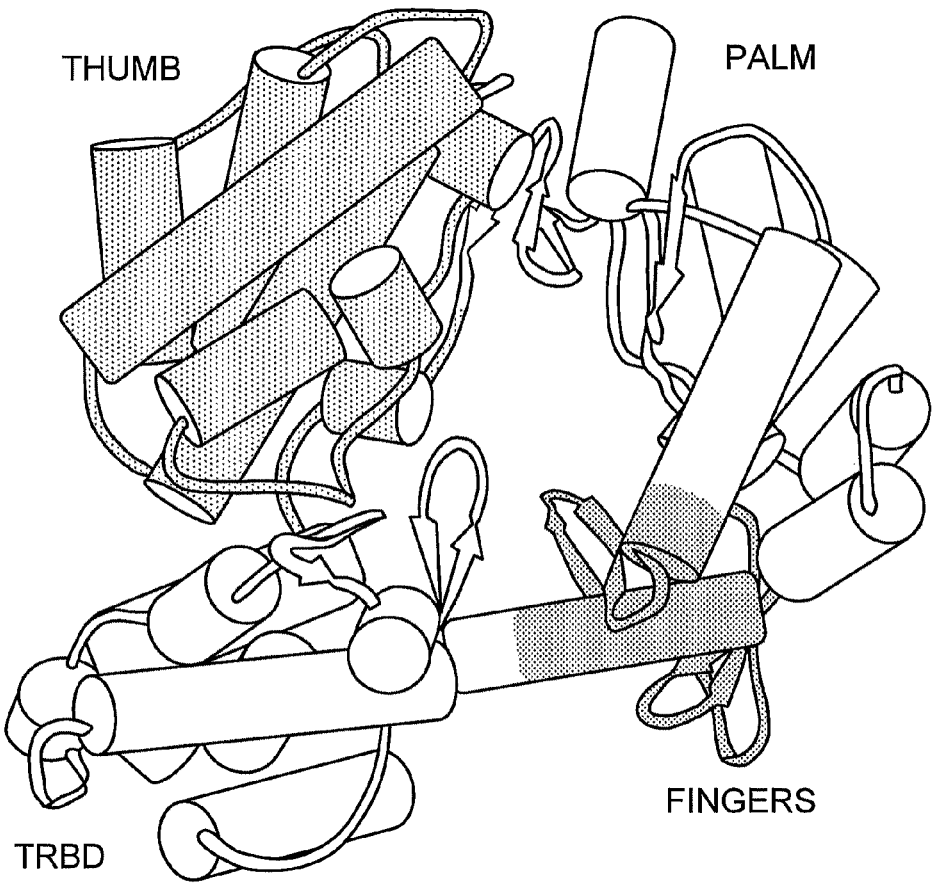
FIG. 1C shows TERT domain organization with the RNA-binding domain (TRBD), the reverse transcriptase domain composed of the "fingers" and "palm" subdomains, and the "thumb" domain depicted.
Figure 2:
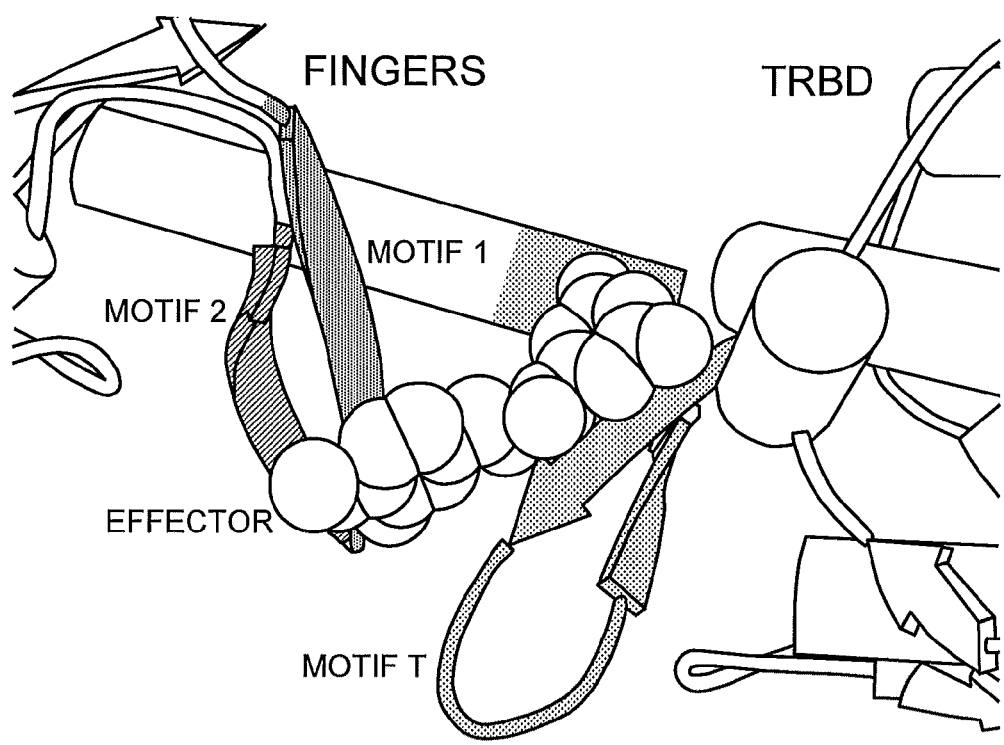
FIG. 2 shows the telomerase T-pocket and drug binding. Conserved motifs T, 1 and 2 that form the T-pocket are shaded.

Telomerase, a ribonucleoprotein complex, replicates the linear ends of eukaryotic chromosomes, thus taking care of the "end of replication problem". TERT contains an essential and universally conserved domain (TRBD; FIG. 1) that makes extensive contacts with the RNA (TER) component of the holoenzyme and this interaction facilitates TERT/TER assembly and repeat addition processivity. The TRBD domain is highly conserved among phylogenetic groups and is essential for the function of telomerase. Extensive biochemical and mutagenesis studies have localized TRBD binding to stem I and the TEB, interactions that are thought to be important for the proper assembly and stabilization of the TERT/TER complex as well as the repeat addition processivity of the holoenzyme. The crystal structure of the catalytic subunit of telomerase showed that the RNA-binding pocket of the RNA-binding domain (TRBD) of telomerase is formed by a highly conserved motif known as the T-motif. The T-motif is located at the interface of the TRBD and the fingers domain and in proximity of the highly conserved motifs 1 and 2 of the "fingers" domain. Together these motifs form a well-defined, deep and solvent exposed pocket (T-pocket) on the surface of the protein (FIG. 2).

Based upon the structure of the T-pocket, an in silico screen was carried out to identify small molecules that associate or interact with this pocket. Compounds were screened for their ability to disrupt the proper association of the catalytic subunit of telomerase TERT with the RNA component TER that binds in this location, thereby modulating telomerase function. Structurally similar groups of compounds, identified via in silico screening as making extensive contacts with motifs T, 1 and 2 of the T-pocket, are listed in Table 1.

TABLE 1

| Group | Compound |
|---|---|
| 1 | 6-[bis(phosphonomethyl)amino]hexanoic acid |
| 2 | (2-{2-[(6-oxo-1,6-dihydro-3-pyridazinyl)carbonyl]carbonohydrazonoyl}phenoxy)acetic Acid |
|  | 3,5-dihydroxy-N'-(3-hydroxy-4-methoxybenzylidene)benzohydrazide |
|  | 2-hydroxy-N'-(3-hydroxy-4-methoxybenzylidene)benzohydrazide |
|  | N'-(3-bromo-4-hydroxy-5-methoxybenzylidene)-3,4-dihydroxybenzohydrazide |
|  | 4-(2-{1-[3-(aminocarbonyl)-4-hydroxyphenyl]ethylidene}hydrazino)benzoic acid |
|  | 4-(2-{oxo[(1-phenylethyl)amino]acetyl}carbonohydrazonoyl)benzoic acid |
|  | 3-hydroxy-N'-(4-hydroxy-3,5-dimethoxybenzylidene)benzohydrazide |
|  | N'-[1-(2,4-dihydroxyphenyl)ethylidene]-4-(2-oxo-1-pyrrolidinyl) benzohydrazide |
| 3 | 5-{[(4-methoxyphenyl)acetyl]amino}isophthalic acid |
|  | phenyl 2-hydroxy-4-[(phenoxyacetyl)amino]benzoate |
|  | 4,4'-[iminobis(methylene)]dibenzoic acid |
|  | 2,2'-[1,3-phenylenebis(carbonylimino)]bis(5-hydroxybenzoic acid) |
|  | 3-{[3-(2-furoylamino)benzoyl]amino}-2-methylbenzoic acid |
|  | phenyl 3-({[4-(propionylamino)benzoyl]oxy}methyl)benzoate |
|  | 4-{[(8-allyl-2-oxo-2H-chromen-3-yl)carbonyl]amino}benzoic acid |
|  | 2,5-bis[(phenylacetyl)amino]terephthalic acid |
|  | 5-{[(2-naphthyloxy)acetyl]amino}isophthalic acid |
|  | 4-[({3-[(tetrahydro-2-furanylcarbonyl)amino]phenyl}amino)carbonyl]benzoic acid |
|  | 5-{[(3,4-dimethylphenoxy)acetyl]amino}-2-hydroxybenzoic acid |

TABLE 1-continued

| Group | Compound |
|---|---|
| | (4-{[4-(2-furoylamino)benzoyl]amino}phenyl)acetic acid |
| | 3,4-dimethyl-6-{[(4-{[(3-pyridinylmethyl)amino]carbonyl}phenyl)amino]carbonyl}-3-cyclohexene-1-carboxylic acid |
| | 6-({[4-(methoxycarbonyl)phenyl]amino}carbonyl)-3,4-dimethyl-3-cyclohexene-1-carboxylic acid |
| | N-[4-(acetylamino)phenyl]-8-allyl-2-oxo-2H-chromene-3-carboxamide |
| | 5-bromo-2-[(4-{[(phenylthio)acetyl]amino}benzoyl)amino]benzoic acid |
| | N-(4-acetylphenyl)-8-allyl-2-oxo-2H-chromene-3-carboxamide |
| | N-[4-(acetylamino)phenyl]-N'-benzylethanediamide |
| | 5-{[(3-methoxyphenoxy)acetyl]amino}isophthalic acid |
| | 2-({3-[(4-carboxybutanoyl)amino]benzoyl}amino)benzoic acid |
| | 6-({[4-(ethoxycarbonyl)phenyl]amino}carbonyl)-3,4-dimethyl-3-cyclohexene-1-carboxylic acid |
| | 1-(4-{[(4-chlorophenyl)acetyl]amino}phenyl)-N-(4-methoxyphenyl)cyclopentanecarboxamide |
| | 3-({[(4-sec-butoxybenzoyl)amino]carbonothioyl}amino)benzoic acid] |
| | N,N'-di-2-naphthylterephthalamide |
| | ethyl 4-{[(5-bromo-4-formyl-2-methoxyphenoxy)acetyl]amino}benzoate |
| | 4,4'-[1,4-phenylenebis(carbonylimino)]dibenzoic acid |
| 4 | N-(3-hydroxyphenyl)-3-phenylacrylamide |
| | 3-(2-chlorophenyl)-N-(3-hydroxyphenyl)acrylamide |
| | 2-bromo-N-{4-[3-(4-methoxyphenyl)acryloyl]phenyl}benzamide |
| | N-[1-{[(4-acetylphenyl)amino]carbonyl}-2-(1,3-benzodioxol-5-yl)vinyl]-2-Chlorobenzamide |
| | 4-(4-hydroxy-3-methoxyphenyl)-N-(4-methoxyphenyl)-6-methyl-2-oxo-1,2,3,4-tetrahydro-5-pyrimidinecarboxamide |
| 5 | N-(2,4-dioxo-1,2,3,4-tetrahydro-5-pyrimidinyl)-2-(3-methoxyphenyl)-1,3-dioxo-5-isoindolinecarboxamide |
| | 5-bromo-2-{[(2-cyclohexyl-1,3-dioxo-2,3-dihydro-1H-isoindol-5-yl)carbonyl]amino}benzoic acid |
| | 5-{[3-(1,3-dioxo-1,3-dihydro-2H-isoindol-2-yl)benzoyl]amino}isophthalic acid |
| | 5-({[2-(2-methoxyethyl)-1,3-dioxo-2,3-dihydro-1H-isoindol-5-yl]carbonyl}amino)isophthalic acid |
| 6 | 3-hydroxy-1-(1-naphthylmethyl)-3-[2-oxo-2-(3-pyridinyl)ethyl]-1,3-dihydro-2H-indol-2-one |
| | N-(4-methoxyphenyl)-2-{[1-(2-methylphenyl)-2,5-dioxo-3-pyrrolidinyl]thio}acetamide |
| | 3-hydroxy-3-[2-(4-methoxyphenyl)-2-oxoethyl]-1-(4-morpholinylmethyl)-1,3-dihydro-2H-indol-2-one |
| | 5-chloro-1-(2-chlorobenzyl)-3-hydroxy-3-[2-oxo-2-(4-pyridinyl)ethyl]-1,3-dihydro-2Hindol-2-one |
| | 3-hydroxy-3-[2-(4-methoxyphenyl)-2-oxoethyl]-1-propyl-1,3-dihydro-2H-indol-2-one |
| | 3-[2-(1,3-benzodioxol-5-yl)-2-oxoethyl]-5-chloro-3-hydroxy-1-(4-methylbenzyl)-1,3-dihydro-2H-indol-2-one |
| | 3-hydroxy-3-[2-(4-methoxyphenyl)-2-oxoethyl]-1-methyl-1,3-dihydro-2H-indol-2-one |
| | 3-[2-(1,3-benzodioxol-5-yl)-2-oxoethyl]-3-hydroxy-1,3-dihydro-2H-indol-2-one |
| | 3-[2-(1,3-benzodioxol-5-yl)-2-oxoethyl]-3-hydroxy-1-(3-phenyl-2-propen-1-yl)-1,3-dihydro-2H-indol-2-one |
| | 5-bromo-3-hydroxy-3-[2-(4-methoxyphenyl)-2-oxoethyl]-1-methyl-1,3-dihydro-2H-indol-2-one |
| | N-(4-methoxyphenyl)-2-{[1-(2-methylphenyl)-2,5-dioxo-3-pyrrolidinyl]thio}acetamide |
| | 3-[2-(1,3-benzodioxol-5-yl)-2-oxoethyl]-3-hydroxy-6,7-dimethyl-1,3-dihydro-2H-indol-2-one |
| 7 | 5-{[(3-amino-4-chlorophenyl)sulfonyl]amino}isophthalic acid |
| | 3-[(3-{[(4-carboxyphenyl)amino]sulfonyl}benzoyl)amino]benzoic acid |
| 8 | 2-([1]benzofuro[3,2-d]pyrimidin-4-ylthio)-N-(3-hydroxyphenyl)acetamide |
| | N-(3-hydroxyphenyl)-2-[(6-methylthieno[2,3-d]pyrimidin-4-yl)thio]acetamide |
| | 2-{[7-(2-furylmethyl)-5,6-dimethyl-7H-pyrrolo[2,3-d]pyrimidin-4-yl]thio}-N-(3-hydroxyphenyl)acetamide |
| | N-[4-(1,3-benzothiazol-2-ylmethoxy)-2-methylphenyl]-2-(3-methylphenoxy)acetamide |
| | 2-{[5-(2-hydroxyethyl)-4-methyl-6-oxo-1,6-dihydro-2-pyrimidinyl]thio}-N-(3-methoxyphenyl)acetamide |
| | N-(3-acetylphenyl)-2-[(5,6-dimethylthieno[2,3-d]pyrimidin-4-yl)thio]acetamide |
| 9 | N-({5-[(2-amino-2-oxoethyl)thio]-4-methyl-4H-1,2,4-triazol-3-yl}methyl)-2-(4-methoxyphenyl)acetamide |
| | N-(3-hydroxyphenyl)-2-{[4-methyl-5-(1-phenoxyethyl)-4H-1,2,4-triazol-3-yl]thio}acetamide |
| | 2,4-dichloro-N-{1-[5-({2-[(4-methoxyphenyl)amino]-2-oxoethyl}thio)-4-methyl-4H-1,2,4-triazol-3-yl]ethyl}benzamide |
| 10 | methyl 2-{[({1-[4-(methoxycarbonyl)phenyl]-1H-tetrazol-5-yl}thio)acetyl]amino}benzoate |
| 11 | 2'-{[(6-methoxy-1,3-benzothiazol-2-yl)amino]carbonyl}-2-biphenylcarboxylic acid |
| | 2-{[4-amino-5-(phenoxymethyl)-4H-1,2,4-triazol-3-yl]thio}-N-1,3-benzothiazol-2-ylacetamide |
| | 2-[(5-oxo-4-phenyl-4,5-dihydro-1H-1,2,4-triazol-3-yl)thio]-N-1,3-thiazol-2-ylpropanamide |
| | 2'-{[(6-ethoxy-1,3-benzothiazol-2-yl)amino]carbonyl}-2-biphenylcarboxylic acid |
| 12 | 4-[(4-{[3-(4-chlorophenyl)-2,4-dioxo-1,3-thiazolidin-5-ylidene]methyl}phenoxy)methyl]benzoic acid |
| | 3-[5-(4-ethoxybenzylidene)-4-oxo-2-thioxo-1,3-thiazolidin-3-yl]benzoic acid |
| | methyl 4-({4-oxo-3-[4-oxo-4-(1,3-thiazol-2-ylamino)butyl]-2-thioxo-1,3-thiazolidin-5-ylidene}methyl)benzoate |
| 13 | 4-[5-[4-(allyloxy)-3-chloro-5-methoxybenzylidene]-2,4,6-trioxotetrahydro-1(2H)-pyrimidinyl]benzoic acid |
| | methyl 4-[5-(3-bromo-5-ethoxy-4-hydroxybenzylidene)-2,4,6-trioxotetrahydro-1(2H)-pyrimidinyl]benzoate |
| | 4-[5-(4-hydroxy-3-methoxybenzylidene)-2,4,6-trioxotetrahydro-1(2H)-pyrimidinyl]benzoic acid |
| | 2-chloro-4-(5-{[1-(2-fluorobenzyl)-2,5-dioxo-4-imidazolidinylidene]methyl}-2-furyl)benzoic acid |
| | methyl 4-[5-(4-hydroxy-3-methoxybenzylidene)-2,4,6-trioxotetrahydro-1(2H)-pyrimidinyl]benzoate |
| | 4-({4-[(1,3-dimethyl-4,6-dioxo-2-thioxotetrahydro-5(2H)-pyrimidinylidene)methyl]phenoxy}methyl)benzoic acid |
| | 4-[5-[4-(allyloxy)-3-methoxybenzylidene]-2,4,6-trioxotetrahydro-1(2H)-pyrimidinyl]benzoic acid |
| | 4-({4-[(1-ethyl-5-oxo-2-thioxo-4-imidazolidinylidene)methyl]phenoxy}methyl)benzoic acid |
| | 4-[5-[3-methoxy-4-(2-propyn-1-yloxy)benzylidene]-2,4,6-trioxotetrahydro-1(2H)-pyrimidinyl]benzoic acid |
| | 4-[5-(3-methoxy-4-propoxybenzylidene)-2,4,6-trioxotetrahydro-1(2H)-pyrimidinyl]benzoic acid |
| | 4-(5-{[1-(2-fluorobenzyl)-2,5-dioxo-4-imidazolidinylidene]methyl}-2-furyl)benzoic acid |
| | 4-[5-[3-bromo-5-methoxy-4-(2-propyn-1-yloxy)benzylidene]-2,4,6-trioxotetrahydro-1(2H)-pyrimidinyl]benzoic acid |
| | methyl 4-[5-(3-methoxybenzylidene)-2,4,6-trioxotetrahydro-1(2H)-pyrimidinyl]benzoate |
| 14 | 3-[(5-{[5-(2,5-dichlorophenyl)-2-furyl]methylene}-4-oxo-1,3-thiazolidin-2-ylidene)amino]benzoic acid |
| | 3-{5-[(2-imino-4-oxo-1,3-thiazolidin-5-ylidene)methyl]-2-furyl}benzoic acid |
| | 3-(5-{[5-imino-2-(2-methylphenyl)-7-oxo-5H-[1,3,4]thiadiazolo[3,2-a]pyrimidin-6(7H)-ylidene]methyl}-2-furyl)benzoic acid |
| 15 | 5-({[2-(4-methoxyphenyl)ethyl]amino}methylene)-2,4,6(1H,3H,5H)-pyrimidinetrione |
| 16 | 5-{[1-(2-chlorophenyl)-2,5-dioxo-3-pyrrolidinyl]amino}-2,4(1H,3H)-pyrimidinedione |
| 17 | 4-formylphenyl (2,4-dioxo-1,3-thiazolidin-5-yl)acetate |
| | 4-formyl-2-methoxyphenyl (2,4-dioxo-1,3-thiazolidin-5-yl)acetate |
| 18 | disodium 7-hydroxy-6-sulfo-1,3-naphthalenedisulfonate |
| | disodium 4-hydroxy-5-sulfo-2,7-naphthalenedisulfonate |
| | sodium 4-amino-5-sulfo-2-naphthalenesulfonate |
| 19 | 2,2'-{[(4-methoxyphenyl)sulfonyl]imino}diacetic acid |

These compounds, as well as derivatives and analogs thereof, are expected to modulate the activity of telomerase. Accordingly, the present invention relates to effector compounds selected for interacting with motifs T, 1 and 2 of the T-pocket of telomerase. In particular embodiments, a compound of the invention is selected from the group listed in Table 1. In another embodiment, one or more of the compounds listed in Table 1 serve as lead compounds for designing or generating derivatives or analogs which are more potent, more specific, less toxic and more effective than known inhibitors of telomerase or the lead compound. Derivatives or analogs can also be less potent but have a longer half-life in vivo and/or in vitro and therefore be more effective at modulating telomerase activity in vivo and/or in vitro for prolonged periods of time.

Derivatives or analogs of the compounds disclosed herein typically contain the essential elements of the parent compound, but have had one or more atoms (e.g., halo, lower alkyl, hydroxyl, amino, thiol, or nitro), or group of atoms (e.g., amide, aryl, heteroaryl, allyl, or propargyl), replaced or added. Such replacements or substitutions can include substituent R groups and/or atoms of the core structure, e.g., replacing a carbon with a heteroatom such as a nitrogen, oxygen, or sulfur. In this regard, the compounds disclosed herein serve as lead compounds for creating a family of derivatives or analogs of use in inhibiting or activating telomerase to, e.g., alter lifespan or proliferative capacity of a cell.

The term "effector" refers to an agonist, antagonist, ligand or other agent that affects the activity of telomerase. Effectors that bind the T-pocket of the TRBD domain and, e.g., sterically block TER binding or block RNP assembly act as effective telomerase-specific inhibitors, whereas effectors that mimic or facilitate TER binding or RNP assembly act as effective telomerase-specific activators.

Figure 3A:
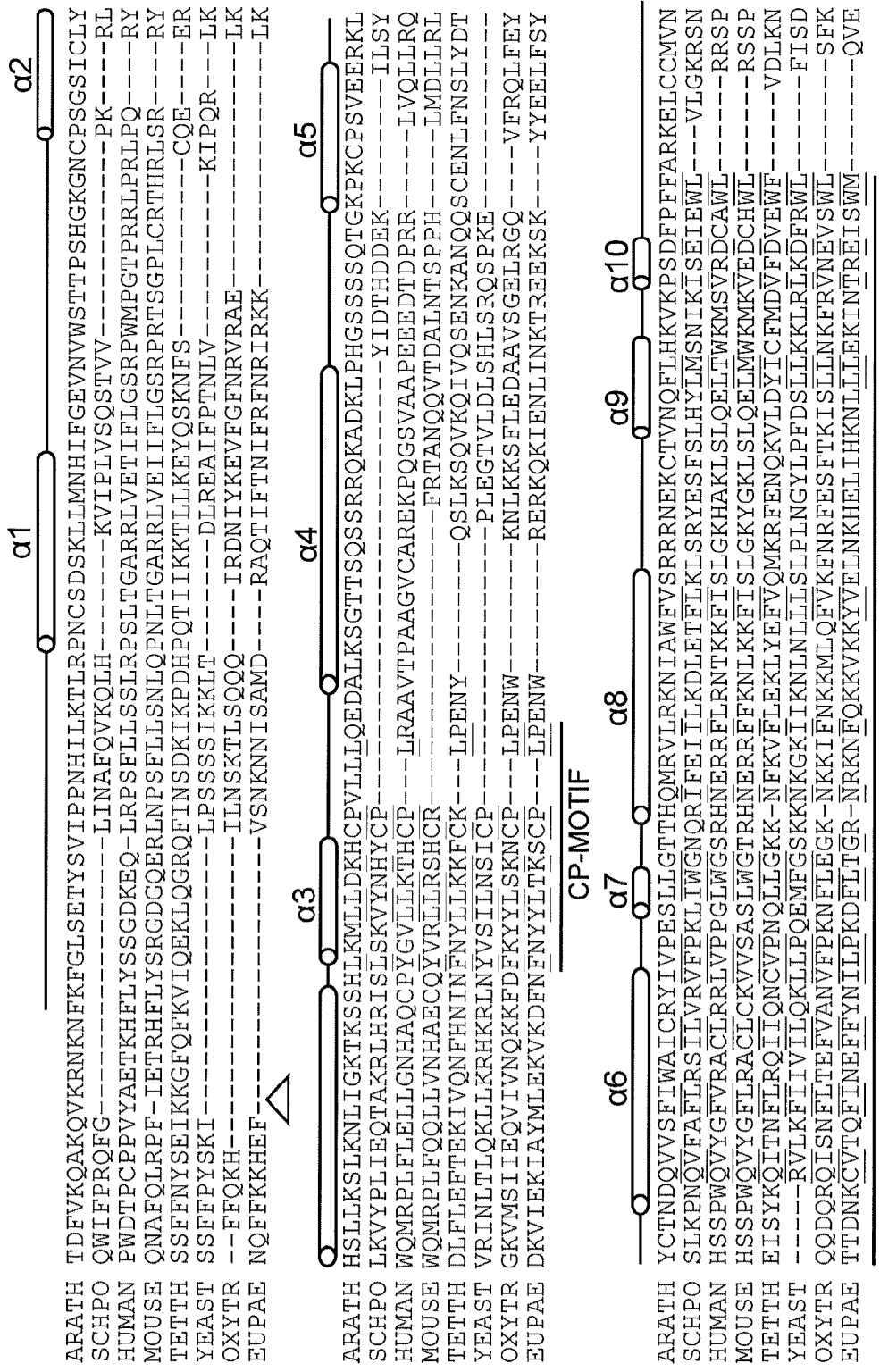
FIGS. 3A and 3B show a sequence alignment and schematic of secondary structure of *Tetrahymena thermophila* TRBDs (TETTH; SEQ ID NO:1) compared with the TRBDs from ciliated protozoa such as, *Euplotes aediculatus* (EUPAE; SEQ ID NO:2) and *Oxytricha trifallax* (OXYTR; SEQ ID NO:3); mammals such as human (SEQ ID NO:4) and mouse (SEQ ID NO:5); fungi such as *Schizosaccharomyces pombe* (SCHPO; SEQ ID NO:6) and *Saccharomyces cerevisiae* (YEAST; SEQ ID NO:7); and plants such as *Arabidopsis thaliana* (ARATH; SEQ ID NO:8) produced by ALSCRIPT Barton (1993) *Protein Eng.* 6:37-40). Conserved residues in key signature motifs are indicated and mutated residues that affect RNA-binding and telomerase function are also indicated. The triangles define the boundaries of the TRBD construct used in the studies herein.
Figure 3B:
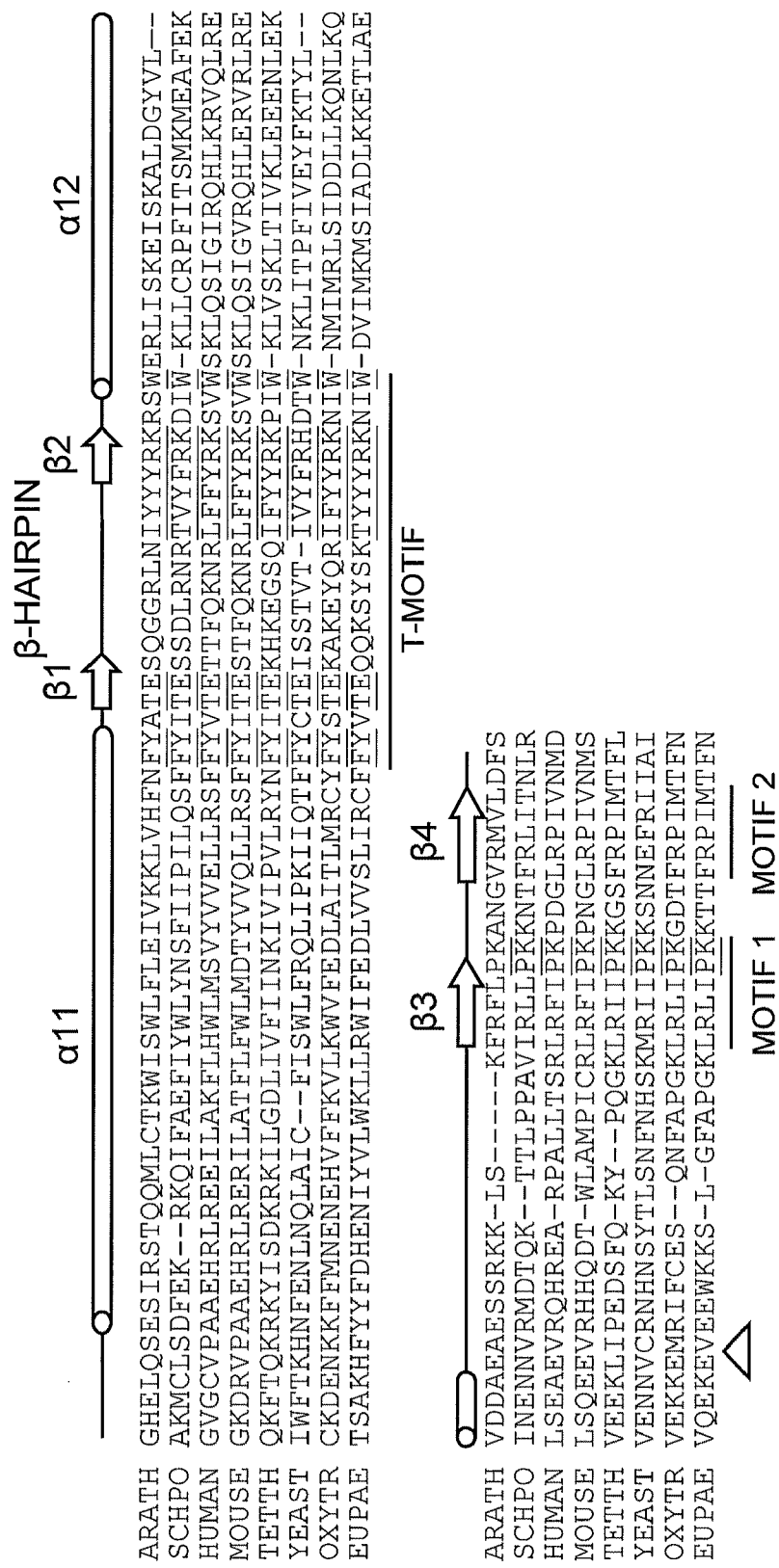

Molecules or compounds of the present invention were selected for interacting with motifs T, 1, and/or 2 of the T-pocket of telomerase. Such selection was based upon various heterogeneous interactions between the compound and telomerase including, but not limited to van der Waals contacts, hydrogen bonding, ionic interactions, polar contacts, or combinations thereof. In this regard, the terms "bind," "binding," "interact," or "interacting" are used interchangeably herein to describe the physical interactions between amino acid residues of motifs T, 1 and/or 2 of telomerase (See FIG. 3) and effectors thereof. In general, the molecules of the invention were selected for interacting with 2, 3, 4, 5, 6 or more of the amino acid residues of the T-pocket of telomerase.

In the context of the present invention, telomerase refers to a family of enzymes which maintain telomere ends by addition of the telomere repeat TTAGGG. Telomerases are described, e.g., by Nakamura, et al. (1997) *Science* 277(5328):955-9 and O'Reilly, et al. (1999) *Curr. Opin. Struct. Biol.* 9(1):56-65. Exemplary telomerase enzymes and the conserved motifs thereof are set forth herein in SEQ ID NOs:1-8 (FIGS. 2A-2B). In addition, full-length sequences for telomerase enzymes are known in the art under GENBANK Accession Nos. AAC39140 (*Tetrahymena thermophila*), NP_197187 (*Arabidopsis thaliana*), NP_937983 (*Homo sapiens*), CAA18391 (*Schizosaccharomyces pombe*), NP_033380 (*Mus musculus*), NP_013422 (*Saccharomyces cerevisiae*), AAC39163 (*Oxytricha trifallax*), CAE75641 (*Euplotes aediculatus*) and NP_001035796 (*Tribolium castaneum*). Reference to telomerase refers to allelic and synthetic variants of telomerase, as well as fragments of telomerase.

The effector activity of compounds of the invention toward telomerase can be confirmed using any conventional assay for measuring telomerase activity. For example, such assays include combining telomerase, the telomerase TRBD domain (e.g., as disclosed herein), or other fragments of telomerase (e.g., motifs or pockets disclosed herein) with or without substrates or cofactors (e.g., TER, complementary DNA, nucleotides, or Mg) in solution and determining whether a test compound can block or enhance telomerase activity. Such activities of telomerase include telomerase catalytic activity (which may be either processive or non-processive activity); telomerase processivity; conventional reverse transcriptase activity; nucleolytic activity; primer or substrate (telomere or synthetic telomerase substrate or primer) binding activity; dNTP binding activity; RNA (i.e., TER) binding activity; and protein binding activity (e.g., binding to telomerase-associated proteins, telomere-binding proteins, or to a protein-telomeric DNA complex). See, e.g., assays disclosed in U.S. Pat. No. 7,262,288.

Telomerase catalytic activity is intended to encompass the ability of telomerase to extend a DNA primer that functions as a telomerase substrate by adding a partial, one, or more than one repeat of a sequence (e.g., TTAGGG) encoded by a template nucleic acid (e.g., TER). This activity may be processive or non-processive. Processive activity occurs when a telomerase RNP adds multiple repeats to a primer or telomerase before the DNA is released by the enzyme complex. Non-processive activity occurs when telomerase adds a partial, or only one, repeat to a primer and is then released. In vivo, however, a non-processive reaction could add multiple repeats by successive rounds of association, extension, and dissociation. This can occur in vitro as well, but it is not typically observed in standard assays due to the vastly large molar excess of primer over telomerase in standard assay conditions. Conventional assays for determining telomerase catalytic activity are disclosed, for example, in Morin (1989) *Cell* 59:521; Morin (1997) *Eur. J. Cancer* 33:750; U.S. Pat. No. 5,629,154; WO 97/15687; WO 95/13381; Krupp, et al. (1997) *Nucleic Acids Res.* 25:919; Wright, et al. (1995) *Nuc. Acids Res.* 23:3794; Tatematsu, et al. (1996) *Oncogene* 13:2265.

Telomerase conventional reverse transcriptase activity is described in, e.g., Morin (1997) supra, and Spence, et al. (1995) *Science* 267:988. Because telomerase contains conserved amino acid motifs that are required for reverse transcriptase catalytic activity, telomerase has the ability to transcribe certain exogenous (e.g., non-TER) RNAs. A conventional RT assay measures the ability of the enzyme to transcribe an RNA template by extending an annealed DNA primer. Reverse transcriptase activity can be measured in numerous ways known in the art, for example, by monitoring the size increase of a labeled nucleic acid primer (e.g., RNA or DNA), or incorporation of a labeled dNTP. See, e.g., Ausubel, et al. (1989) *Current Protocols in Molecular Biology*, John Wiley & Sons, New York, N.Y.

Because telomerase specifically associates with TER, it can be appreciated that the DNA primer/RNA template for a conventional RT assay can be modified to have characteristics related to TER and/or a telomeric DNA primer. For example, the RNA can have the sequence $(CCCTAA)_n$, where n is at least 1, or at least 3, or at least 10 or more. In one embodiment, the $(CCCTAA)_n$ region is at or near the 5' terminus of the RNA (similar to the 5' locations of template regions in telomerase RNAs). Similarly, the DNA primer may have a 3' terminus that contains portions of the TTAGGG telomere sequence, for example $X_n$TTAG, $X_n$AGGG, etc., where X is a non-telomeric sequence and n is 6-30. In another embodiment, the DNA primer has a 5' terminus that is non-complementary to the RNA template, such that when the primer is annealed to the RNA, the 5' terminus of the primer remains unbound. Additional modifications of standard reverse transcription assays that may be applied to the methods of the invention are known in the art.

Telomerase nucleolytic activity is described in, e.g., Morin (1997) supra and Collins & Grieder (1993) *Genes Dev.* 7:1364. Telomerase preferentially removes nucleotides, usually only one, from the 3' end of an oligonucleotide when the 3' end of the DNA is positioned at the 5' boundary of the DNA template sequence, in humans and *Tetrahymena*, this nucleotide is the first G of the telomeric repeat (TTAGG in humans). Telomerase preferentially removes G residues but has nucleolytic activity against other nucleotides. This activity can be monitored using conventional methods known in the art.

Telomerase primer (telomere) binding activity is described in, e.g., Morin (1997) supra; Collins, et al. (1995) *Cell* 81:677; Harrington, et al. (1995) *J. Biol. Chem.* 270:8893. There are several ways of assaying primer binding activity; however, a step common to most methods is incubation of a labeled DNA primer with telomerase or telomerase/TER under appropriate binding conditions. Also, most methods employ a means of separating unbound DNA from protein-bound DNA. Such methods can include, e.g., gel-shift assays or matrix binding assays. The DNA primer can be any DNA with an affinity for telomerase, such as, for example, a telomeric DNA primer like $(TTAGGG)_n$, where n could be 1-10 and is typically 3-5. The 3' and 5' termini can end in any location of the repeat sequence. The primer can also have 5' or 3' extensions of non-telomeric DNA that could facilitate labeling or detection. The primer can also be derivatized, e.g., to facilitate detection or isolation.

Telomerase dNTP binding activity is described in, e.g., Morin (1997) supra and Spence, et al. (1995) supra. Telomerase requires dNTPs to synthesize DNA. The telomerase protein has a nucleotide binding activity and can be assayed for dNTP binding in a manner similar to other nucleotide binding proteins (Kantrowitz, et al. (1980) *Trends Biochem. Sci.* 5:124). Typically, binding of a labeled dNTP or dNTP analog can be monitored as is known in the art for non-telomerase RT proteins.

Telomerase RNA (i.e., TER) binding activity is described in, e.g., Morin (1997) supra; Harrington, et al. (1997) *Science* 275:973; Collins, et al. (1995) *Cell* 81:677. The RNA binding activity of a telomerase protein of the invention may be assayed in a manner similar to the DNA primer binding assay described supra, using a labeled RNA probe. Methods for separating bound and unbound RNA and for detecting RNA are well known in the art and can be applied to the activity assays of the invention in a manner similar to that described for the DNA primer binding assay. The RNA can be full length TER, fragments of TER or other RNAs demonstrated to have an affinity for telomerase or TRBD. See U.S. Pat. No. 5,583,016 and WO 96/40868.

To further evaluate the efficacy of a compound identified using the method of the invention, one of skill will appreciate that a model system of any particular disease or disorder involving telomerase can be utilized to evaluate the adsorption, distribution, metabolism and excretion of a compound as well as its potential toxicity in acute, sub-chronic and chronic studies. For example, the effector or modulatory compound can be tested in an assay for replicative lifespan in *Saccharomyces cerevisiae* (Jarolim, et al. (2004) *FEMS Yeast Res.* 5(2):169-77). See also, McChesney, et al. (2005) *Zebrafish* 1(4):349-355 and Nasir, et al. (2001) *Neoplasia* 3(4):351-359, which describe marine mammal and dog tissue model systems for analyzing telomerase activity.

Compounds disclosed herein find application in a method for modulating (i.e., blocking or inhibiting, or enhancing or activating) telomerase. Such a method involves contacting a telomerase either in vitro or in vivo with an effective amount of a compound of the invention so that the activity of telomerase is modulated. An effective amount of an effector or modulatory compound is an amount which reduces or increases the activity of the telomerase by at least 30%, 40%, 50%, 60%, 70%, 80%, 90% or 100% when compared to telomerase not contacted with the compound. Such activity can be monitored by enzymatic assays detecting activity of the telomerase or by monitoring the expression or activity of proteins which are known to be associated with or regulated by telomerase.

Modulation of telomerase activity finds application in selectively analyzing telomerase signaling events in model systems as well as in preventing or treating diseases, conditions, and disorders involving or associated with telomerase activity or reduction or lack thereof. The selection of the compound for use in preventing or treating a particular disease or disorder will be dependent upon the particular disease or disorder. For example, human telomerase is involved in cancer and therefore a compound which inhibits telomerase is useful in the prevention or treatment of cancer including solid tumors (e.g., adenocarcinoma of the breast, prostate, and colon; melanoma; non-small cell lung; glioma; as well as bone, breast, digestive system, colorectal, liver, pancreatic, pituitary, testicular, orbital, head and neck, central nervous system, acoustic, pelvic, respiratory tract, and urogenital neoplasms) and leukemias (e.g., B-cell, mixed-cell, null-cell, T-cell, T-cell chronic, lymphocytic acute, lymphocytic chronic, mast-cell, and myeloid). Cancer cells (e.g., malignant tumor cells) that express telomerase activity (telomerase-positive cells) can be mortalized by decreasing or inhibiting the endogenous telomerase activity. Moreover, because telomerase levels correlate with disease characteristics such as metastatic potential (e.g., U.S. Pat. Nos. 5,639,613; 5,648,215; 5,489,508; Pandita, et al. (1996) *Proc. Am. Ass. Cancer Res.* 37:559), any reduction in telomerase activity could reduce the aggressive nature of a cancer to a more manageable disease state (increasing the efficacy of traditional interventions).

By way of illustration, Example 2 describes cell-based assays and animal model systems which are useful for assessing the inhibition of tumor cell growth by one or more compounds of the invention. Another useful method for assessing anticancer activities of compounds of the invention involves the multiple-human cancer cell line screening assays run by the National Cancer Institute (see, e.g., Boyd (1989) in *Cancer: Principles and Practice of Oncology Updates*, DeVita et al., eds, pp. 1-12). This screening panel, which contains approximately 60 different human cancer cell lines, is a useful indicator of in vivo antitumor activity for a broad variety of tumor types (Grever, et al. (1992) *Seminars Oncol.* 19:622; Monks, et al. (1991) *Natl. Cancer Inst.* 83:757-766), such as leukemia, non-small cell lung, colon, melanoma, ovarian, renal, prostate, and breast cancers. Antitumor activities can be expressed in terms of $ED_{50}$ (or $GI_{50}$), where $ED_{50}$ is the molar concentration of compound effective to reduce cell growth by 50%. Compounds with lower $ED_{50}$ values tend to have greater anticancer activities than compounds with higher $ED_{50}$ values.

Upon the confirmation of a compound's potential activity in one or more in vitro assays, further evaluation is typically conducted in vivo in laboratory animals, for example, measuring reduction of lung nodule metastases in mice with B16 melanoma (e.g., Schuchter, et al. (1991) *Cancer Res.* 51:682-687). The efficacy of a compound of the invention either alone or as a drug combination chemotherapy can also be evaluated, for example, using the human B-CLL xenograft model in mice (e.g., Mohammad, et al. (1996) *Leukemia* 10:130-137). Such assays typically involve injecting primary tumor cells or a tumor cell line into immune compromised mice (e.g., a SCID mouse or other suitable animal) and allowing the tumor to grow. Mice carrying the tumors are then treated with the compound of interest and tumor size is measured to follow the effect of the treatment. Alternatively, the compound of interest is administered prior to injection of tumor cells to evaluate tumor prevention. Ultimately, the safety and efficacy of compounds of the invention are evaluated in human clinical trials.

Compounds that activate or stimulate telomerase activity find application in methods for treating or preventing a disease or condition wherein telomerase activity is lacking or reduced, e.g., conditions relating to the proliferative capacity of cells, conditions resulting from cell damage or death, or conditions associated with cellular senescence. As such stimulatory compounds find use in methods for decreasing the rate of senescence of a subject, e.g., after onset of senescence; for extending the lifespan of a subject; or for treating or preventing a disease or condition relating to lifespan. Certain diseases of aging are characterized by cell senescence-associated changes due to reduced telomere length (compared to younger cells), resulting from the absence (or much lower levels) of telomerase activity in the cell. Telomerase activity and telomere length can be increased by, for example, increasing the activity of telomerase in the cell. A partial listing of conditions associated with cellular senescence in which increased telomerase activity can be therapeutic includes Alzheimer's disease, Parkinson's disease, Hunington's disease, and stroke; age-related diseases of the integument such as dermal atrophy, elastolysis and skin wrinkling, graying of hair and hair loss, chronic skin ulcers, and age-related impairment of wound healing; degenerative joint disease; osteoporosis; age-related immune system impairment (e.g., involving cells such as B and T lymphocytes, monocytes, neutrophils, eosinophils, basophils, NK cells and their respective progenitors); age-related diseases of the vascular system; diabetes; and age-related macular degeneration. Moreover, telomerase activators can be used to increase the proliferative capacity of a cell or in cell immortalization, e.g., to produce new cell lines (e.g., most human somatic cells).

Prevention or treatment typically involves administering to a subject in need of treatment a pharmaceutical composition containing an effective of a compound of the invention. In most cases this will be a human being, but treatment of agricultural animals, e.g., livestock and poultry, and companion animals, e.g., dogs, cats and horses, is expressly covered herein. The selection of the dosage or effective amount of a compound is that which has the desired outcome of preventing, reducing or reversing at least one sign or symptom of the disease or disorder being treated. Methods for treating cancer and other telomerase-related diseases in humans are described in U.S. Pat. Nos. 5,489,508, 5,639,613, and 5,645,986. By way of illustration, a subject with cancer (including, e.g., carcinomas, melanomas, sarcomas, lymphomas and leukaemias) can experience unexplained weight loss, fatigue, fever, pain, skin changes, sores that do not heal, thickening or lump in breast or other parts of the body, or a nagging cough or hoarseness, wherein treatment with a compound of the invention can prevent, reduce, or reverse one or more of these symptoms.

Pharmaceutical compositions can be in the form of pharmaceutically acceptable salts and complexes and can be provided in a pharmaceutically acceptable carrier and at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically-acceptable carrier, composition or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the subject being treated.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Compounds of the present invention can be used alone or in combination with other agents, such as cancer chemotherapeutic agents, in the treatment of disease. Thus, in particular embodiments, the present invention embraces combining an effective amount of a compound of the invention with one or more chemotherapeutic agents or antiproliferative agents. The drug combination can be included in the same or multiple pharmaceutical compositions. In addition, the individual drugs can be administered simultaneously or consecutively (e.g., immediately following or within an hour, day, or month of each other).

The compositions of the present invention can be administered parenterally (for example, by intravenous, intraperitoneal, subcutaneous or intramuscular injection), topically (including buccal and sublingual), orally, intranasally, intravaginally, or rectally according to standard medical practices.

The selected dosage level will depend upon a variety of factors including the activity of the particular compound of the present invention employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of a compound at levels lower than that required in order to achieve the desired therapeutic effect and gradually increase the dosage until the desired effect is achieved. This is considered to be within the skill of the artisan and one can review the existing literature on a specific compound or similar compounds to determine optimal dosing.

The invention is described in greater detail by the following non-limiting examples.

EXAMPLE 1

Structure of *Tetrahymena thermophila* TERT

Protein Expression and Purification. The *T. thermophila* TERT residues 254-519 was identified by limited proteolysis and cloned into a modified version of the pET28b vector containing a cleavable hexa-histidine tag at its N-terminus. The protein was over-expressed in *E. coli* BL21 (pLysS) at 20° C. for 4 hours. The cells were lysed by sonication in 50 mM Tris-HCl, 10% glycerol, 0.5 M KCl, 5 mM β-mercaptoethanol, and 1 mM PMSF, pH 7.5 on ice. The protein was first purified over a Ni-NTA column followed by TEV cleavage of the hexa-histidine tag overnight at 4° C. The TRBD/TEV mix was diluted so that the concentration of imidazole was at 15 mM and the protein mix was passed over a Ni-NTA column to remove the TEV, the cleaved tag and any tagged protein. The Ni-NTA flow through was concentrated to 1 ml and diluted to a salt concentration of 0.15 M. The diluted TRBD sample was then passed over a POROS-HS column (PerSeptive Biosystems, Framingham, Mass.). At this stage, the protein was more than 99% pure. The protein was finally passed over a SEPHADEX-S200 sizing column pre-equilibrated with 50 mM Tris-HCl, 10% glycerol, 0.5 M KCl, and 2 mM DTT, pH 7.5 to remove any TRBD aggregates. The pure, monodisperse protein as indicated by SDS-page and dynamic light scattering, respectively, was concentrated to 8 mg/ml using an AMICON 10K cutoff (MILLIPORE, Billerica, Mass.) and the protein was stored at 4° C. for subsequent studies. Stock protein was dialyzed in 5 mM Tris-HCl, 500 mM KCl, 1 mM TCEP, pH 7.5 prior to crystallization trials.

Protein Crystallization and Data Collection. Initial plate-like clusters of TRBD that diffracted poorly (~4 Å resolution) were grown at 4° C. using the sitting drop method by mixing on volume of dialyzed protein with one volume of reservoir solution containing 20% PEG 3350, 0.2 M NaNO$_3$. Single, well diffracting crystals were grown in microbatch trays under paraffin oil by mixing one volume of dialyzed protein with an equivalent volume of 50 mM HEPES (pH 7.0), 44% PEG 400, 0.4 M NaNO$_3$, 0.4 M NaBr and 1 mM TCEP at 4° C. Crystals were harvested into cryoprotectant solution that contained 25 mM HEPES (pH 7.0), 25% PEG 400, 0.2 M NaNO$_3$, 0.2 M NaBr and 1 mM TCEP and were flash frozen in liquid nitrogen. Data were collected at the NSLS, beam line X6A and processed with HKL-2000 (Minor (1997) *Meth. Enzymol. Macromole. Crystallogr. Part A* 276:307-326) (Table 2). The crystals belong to the monoclinic space group P2$_1$ with one monomer in the asymmetric unit.

TABLE 2

| TRBD$_{(254-519)}$ | Native | Holmium-Derivative | |
| --- | --- | --- | --- |
| | λ | Ho-λ1 | Ho-λ2 |
| Wavelength (Å) | 0.9795 | 1.5347 | 1.5595 |
| Space group | P2$_1$ | P2$_1$ | P2$_1$ |

TABLE 2-continued

| TRBD$_{(254-519)}$ | Native | Holmium-Derivative | |
| --- | --- | --- | --- |
| | λ | Ho-λ1 | Ho-λ2 |
| Cell dimensions (Å) | 39.4 | 39.2 | 39.2 |
| | 67.2 | 68.2 | 68.2 |
| | 51.5 | 50.1 | 50.1 |
| | 90.7 | 91.6 | 91.6 |
| Resolution (Å) | 20-1.71 | 50-2.59 | 50-2.63 |
| | (1.77-1.71)* | (2.69-2.59) | (3.02-2.63) |
| Redundancy | 3.7 (3.0) | 1.7 (1.8) | 1.7 (1.8) |
| Completeness (%) | 99.3 (93.3) | 92.5 (88.1) | 92.9 (88.7) |
| R$_{sym}$ (%) | 4.7 (48.1) | 7.3 (23.8) | 7.0 (21.5) |
| I/σ (I) | 27.3 (2.6) | 9 (3.4) | 9.4 (3.7) |

Phasing Analysis
Resolution (Å) 50-2.7
Number of sites 2
Mean figure of merit (FOM) 0.43
*Values in parentheses correspond to the highest resolution shell.

Structure Determination and Refinement. Initial phases were obtained from a two-wavelength MAD holmium (Ho) derivative that was prepared by co-crystallizing the protein with 5 mM HoCl$_3$. Heavy atom sites were located using SOLVE (Terwilliger (2003) *Methods Enzymol.* 374:22-37) and the sites were refined and new phases calculated with MLPHARE (CCP4 (1994) *Acta Crystallogr. D* 50:760-763) as implemented in ELVES (Holton & Alber (2004) *Proc. Natl. Acad. Sci. USA* 101:1537-1542) (Table 2). Initial maps showed well-defined density only for the larger half of the molecule. The density for the smaller half of the molecule was weak mostly due to its intrinsic mobility with respect to larger half of the molecule. The problem associated with building the model into the density was exacerbated by the lack of information regarding the location of specific side chains such as selenomethionines. Key factors in building a complete model were successive rounds of PRIME and SWITCH in RESOLVE (Terwilliger (2002) *Acta Crystallogr. D Biol. Crystallogr.* 58:1937-1940) followed by manual building in COOT (Emsley & Cowtan (2004) *Acta Crystallogr. D Biol. Crystallogr.* 60:2126-2132). The model was refined using both CNS-SOLVE (Brunger, et al. (1998) *Acta Crystallogr. D Biol. Crystallogr.* 54:905-921) and REFMAC5 (Murshudov, et al. (1997) *Acta Crystallogr. D Biol. Crystallogr.* 53:240-255). The last cycles of refinement were carried out with TLS restraints as implemented in REFMAC5 (Table 3). Figures were prepared in PYMOL (DeLano (2002)) and electrostatic surfaces in APBS (Baker, et al. (2001) *Proc. Natl. Acad. Sci. USA* 98:10037-10041).

TABLE 3

| TRBD$_{(254-519)}$ | |
| --- | --- |
| Refinement Statistics | |
| Resolution (Å) | 20-1.71 |
| R$_{work}$/R$_{free}$ (%) | 20.0/23.9 |
| RMSD bonds (Å) | 0.008 |
| RMSD angles (°) | 0.831 |
| Number of atoms | |
| Protein | 2145 |
| Bromine | 7 |
| Water | 213 |
| Average B (Å$^2$) | |
| Protein | 27.41 |
| Bromine | 42.63 |
| Water | 31.22 |

TABLE 3-continued

TRBD$_{(254-519)}$

| Ramachandran % (no res.) | |
|---|---|
| Most favored | 91.6 |
| Allowed | 8.4 |

TRBD Structure. To explore the role of the essential RNA-binding domain of telomerase (TRBD), a construct identified by limited proteolysis, containing residues 254-519 from *T. thermophila* (FIG. 1A) was purified to homogeneity. This protein construct was monomeric in solution as indicated by both gel filtration and dynamic light scattering. Crystals of this construct grew readily and diffracted to 1.71 Å resolution (Table 3). The protein was phased to 2.7 Å resolution by the multiwavelength anomalous dispersion method (MAD) using a holmium derivative and the phases were extended with the native dataset to 1.71 Å resolution (Table 3). In the refined structure there was clear density for residues 257-266 and 277-519.

The structure contains twelve α-helices linked together by several long loops and two short β-strands. The helices are organized so that the molecule is divided into two asymmetric halves linked together by three extended loops. The larger half is composed of nine α-helices, one of which (α11) runs along the middle of the domain and spans its entire length making contacts with all other eight helices. The smaller half of the molecule is composed of three helices (α4, α5 and α12), all of which are arranged at a ~120° angle to the plane of the larger half of the protein. The smaller half of the protein is somewhat more flexible than the larger half as suggested by its high B factors reflecting the intrinsic mobility of this region and may result from the absence of observable contacts with the RNA substrate. An interesting feature of the structure is a β-hairpin formed by the 15-residues that connect helices α11 and α12 of the larger and the smaller halves, respectively. The β-hairpin protrudes from the base of the crevice formed by the two halves of the protein and stands at a 45° angle to the plane of the smaller half of the molecule. The positioning and the fact that this hairpin is well-defined in the density could be attributed to helix α7 and the loop that connects it to helix α8. Both of these elements are conveniently positioned at the back of this hairpin holding it in place. A search in the protein structure database using the Dali server (Holm & Sander (1996) *Science* 273:595-603) produced no structural homologues, indicating that the TRBD domain of telomerase is a novel nucleic acid binding fold. The overall organization of the two halves of the protein has significant implications for nucleic acid recognition and binding.

The TRBD RNA-Binding Motifs. The ability of the TRBD domain to interact with TER has been attributed to two conserved motifs known as the CP-, and T-motifs, while a third motif known as the QFP-motif is thought to be important for RNP assembly (FIGS. 2A and 2B) (Bosoy, et al. (2003) *J. Biol. Chem.* 278:3882-3890; Bryan, et al. (2000) supra; Jacobs, et al. (2005) supra; Xia, et al. (2000) *Mol. Cell. Biol.* 20:5196-5207). The TRBD structure shows that the QFP-motif is formed by several mostly hydrophobic residues, which are located on the larger half of the molecule and are buried within the core of the domain making extensive hydrophobic contacts with the surrounding residues aiding in the fold of the protein. These residues included Gln375, Ile376, Leu380, Ile383, Ile384, Cys387, Val388, Pro389, Leu392, Leu393, Asn397, Leu405, Phe408, Tyr422, Ile423, Met426, Trp433, and Phe434. The location and the contacts of the QFP-residues indicate that they are not directly involved in nucleic acid binding.

The T-motif is located at the center of the molecule where the two halves of the protein meet and it is composed of residues that form both part of the β-hairpin and helix α12. Together these structural elements form a narrow (~10 Å), well-defined pocket (T-pocket) that is lined by several solvent exposed and highly conserved residues (Phe476, Tyr477, Thr479, Glu480, Tyr491, Arg492, Lys493, and Trp496). Of particular note are the side chains of the invariant residues Tyr477 and Trp496, which are part of the β-hairpin and helix α12, respectively. Together these residues form a "hydrophobic pincer" that could sandwich the purine/pirimidine moiety of an interacting RNA nucleotide. In this structure, the side chains of Tyr477 and Trp496 are only 4 Å apart, which is not sufficient to accommodate a nucleotide base. Insertion of a base between the two side chains would require structural rearrangement of the T-pocket, possibly splaying of the two halves of the molecules apart. In addition to its hydrophobic part, the T-pocket also contains several hydrophilic residues such as Arg492 and Lys493 both of which are solvent exposed and are located at the interface of the T- and CP-pocket connecting the two together.

The CP-motif is formed by helix α3 and the following loop. In contrast to the T-motif, which is a narrow well-defined pocket, the CP-motif is composed a shallow, wide (~20 Å), highly positively charged cavity located adjacent and beneath the entry of the T-pocket. Several of the conserved residues that form the CP-motif include Phe323, Leu327, Lys328, Lys329, Cys331, Leu333, and Pro334. These residues are buried in the core of the larger half or the region that connects the two halves of the molecule and are contributing to the protein fold. Of particular interest are residues Leu327, Cys331, Leu333 and Pro334 all of which are buried and make direct contacts with structural elements of the T-motif thus aiding in the formation of both the CP- and the T-pockets. For example, Leu327 and Cys331 are within Van der Waal contacts of the large hydrophobic side chain of the invariant Phe476 and the aliphatic part of the side chain of the conserved Arg492 both of which form part of the β-hairpin. Interestingly, Arg492 is located at the base of helix α12 and its contact with Leu327, Cys331, and Leu333 partially helps position this helix at a 45° angle of the plane that runs parallel with the larger half of the molecule thus further facilitating the formation of the T-pocket. Moreover, the interaction of Arg492 with Leu327, Cys331, and Leu333 helps position the guanidine moiety, the only solvent-exposed part of this residue, at the interface formed by the CP- and T-pockets. The CP-pocket also contains several surface-exposed, conserved residues that are mainly hydrophilic in nature. These include Lys328 and Lys329 both of which are located beneath the T-pocket and in close proximity of Arg492 and Lys493 together forming a single large, positively charged surface area that almost spans the entire side of the molecule.

TRBD Structure and Existing Mutants. Several mutants of TERT that affect RNA-binding and telomerase activity have been isolated. Several of these mutants are found in the TRBD domain and specifically within the T- and CP-motifs. Single- and double- as well as stretches of 4-10 amino acid alanine substitutions within these two motifs showed moderate to severe loss (20-100%) of RNA-binding affinity and polymerase activity when compared to the wild type enzyme (Bryan, et al. (2000) supra; Lai, et al. (2002) supra; Miller, et al. (2000) supra).

One set of mutants, Phe476Ala, Tyr477Ala, Thr479Ala, Glu480Ala, Arg492Ala and Trp496Ala, showed severe loss (80-100%) of RNA-binding affinity and telomerase activity suggesting that these residues mediate direct contacts with the RNA substrate (Bryan, et al. (2000) supra; Lai, et al. (2002) supra). All five residues are part of the T-motif and, with the exception of Phe476, all of their side chains are solvent exposed. In the structure, both Tyr477 and Trp496 are located at the base of the T-pocket and their side chains form a "hydrophobic pincer". Assuming that the solvent-exposed side chains of these residues are involved in stacking interactions with the ssRNA, mutating them to small alanines would likely compromise substrate binding which explains the dramatic loss of RNA-binding affinity and telomerase function. In contrast to Tyr477 and Trp496, Phe476 is buried and is not accessible for interactions with the nucleic acid substrate. Instead, Phe476 is located at the base of the β-hairpin and contributes significantly to the formation of the T-pocket. Mutating the large hydrophobic side chain of this residue to the small alanine would likely lead to conformational rearrangements of this pocket and loss of RNA-binding affinity and telomerase activity.

A second set of alanine mutants, Leu327Ala, Lys329Ala, Cys331Ala, and Pro334Ala, which showed moderate loss of RNA-binding affinity and telomerase activity has also been isolated (Bryan, et al. (2000) supra; Miller, et al. (2000) supra). Both Leu327 and Cys331 make direct contacts with Phe476 and the aliphatic part of the side chain of Arg492, both of which are located at the base of the T-motif. Mutation to the smaller alanine residue could result in the rearrangement of the T-pocket potentially leading to loss of interactions with the nucleic acid substrate and loss of function. Likewise, Pro334 is located at the back of helix α12 and makes direct contacts with residues of this structural element. Helix α12 contains the invariant Trp496 and the conserved Lys493, both of which form part of the T-pocket. Mutating Pro334 into an alanine could lead to the displacement of helix α10 and reorganization of the T-pocket leading to loss of function. Lys329 is also located on helix α3 and unlike Leu327Ala, Cys331Ala, and Pro334Ala, is solvent exposed possibly making direct contacts with the nucleic acid substrate. Mutating it to an alanine would lead to lose of RNA interactions and loss of RNA-binding affinity and telomerase activity.

TRBD Domain-Mediated Formation of Stable RNP Complex and Repeat Addition Processivity. In vivo, telomerase exists as a stable ribonucleoprotein complex and contacts between the protein (TERT) and the RNA components (TER) are mediated by the TEN, TRBD and the RT domains. Extensive biochemical and mutagenesis studies have shown that the TRBD is involved in extensive, specific interactions with stem I and the TBE of TER (Lai, et al. (2001) supra; O'Connor, et al. (2005) supra) (FIG. 4). Contacts between the TRBD and TER are thought to facilitate the proper assembly and stabilization of the RNP complex and promote repeat addition processivity (Lai, et al. (2003) supra). In ciliates, in addition to the TRBD, a conserved motif (CP2) located N-terminally to the TRBD domain is thought to be required for TERT-TER assembly and template boundary definition (Lai, et al. (2002) supra; Miller, et al. (2000) supra). However, until now it has been unclear as to how the telomerase TRBD carries out this process. The present analysis indicates that the TRBD domain is divided into two asymmetric halves connected by several long loops that are shaped like a boomerang, an arrangement that has significant implications for RNA recognition and binding. The overall organization of the two lobes of the molecule results in the formation of two well-defined cavities (CP- and T-pockets) on the surface of the protein that consist of several solvent-exposed, invariant/conserved residues. The T-pocket is a narrow, deep cavity located at the junction of the two halves of the molecule with part of it being hydrophobic in nature while the part that is located in proximity of the CP-pocket is positively charged. Interestingly, the hydrophobic side chains of Tyr477 and Trp496 are solvent-exposed and are stacked against each other forming a narrow "hydrophobic pincer" that in this structure could not accommodate a nucleotide base. It is, however, worth noting that helix α12, which contains Trp496, is somewhat flexible with respect to the β-hairpin that contains Tyr477. The ability of helix α12 and therefore Trp496 to move could splay the two side chains apart thus allowing for the space required for the accommodation of a nucleotide base between them. Another possibility is that the polar moiety of Tyr477 and Trp496 could act together as a nucleotide base that would allow for the formation of pseudo Watson Crick interactions with an incoming nucleotide base. Pseudo Watson Crick interactions have been previously observed for a number of protein nucleic acid complexes including the Rho transcription termination factor (Bogden, et al. (1999) *Mol. Cell.* 3:487-493) and the signal recognition particle (Wild, et al. (2001) *Science* 294:598-601). The width and the organization of the hydrophobic part of the T-pocket indicate that it binds ssRNA, most likely the TBE, possibly mediated by a network of stacking interactions.

In contrast to the T-pocket, the CP-pocket is a positively charged, shallow cavity located on the side of the molecule and forms an extension of the T-pocket. Together the hydrophilic part of the T-pocket and the CP-pocket are lined with several lysines and arginines the side chains of which are solvent exposed and could be involved in direct contacts with the backbone of double-stranded RNA. The width and the chemical nature of this pocket indicate that it binds double-stranded RNA, most likely stem I or stem II (FIG. 4). The nature and the extent of the protein/nucleic acid interactions mediated by the TRBD binding pockets provides the stability required for the proper assembly of a functional ribonucleoprotein enzyme and guide TERT to a TER binding site (between stem I and II) that has significant implications for telomerase function.

Telomerase is unique in its ability to add multiple short oligonucleotide repeats at the end of linear chromosomes. The enzyme's ability to do so has been partly attributed to the interactions of the TRBD domain with the TBE and in ciliates both the TRBD and the CP2 motif (Lai, et al. (2002) supra; Lai, et al. (2003) supra; Miller, et al. (2000) supra). The TBE is composed of stem II and the flanking ssRNA regions and is located downstream of stem I and only a few nucleotides upstream of the RNA template (FIG. 4). The TRBD structure indicates that the T-pocket, a narrow, hydrophobic cavity located on the surface of the protein that can only accommodate ssRNA, may play an important role in this process. Assuming that the T-pocket binds the ssRNA that connects stem I and stem II, this interaction likely forces stem II to act as a steric block, which in turn forces the TRBD domain to stay within the boundaries of stem I and stem II. The stem I- and II-locked TRBD domain then may act as an anchor that constrains the distance the RT domain can travel and prevents it from moving beyond the boundaries of the RNA template thus promoting telomerase addition processivity. In ciliates however, the TRBD domain alone is not sufficient for template boundary definition and it requires the action of the CP2 motif (Lai, et al. (2002) supra; Miller, et al. (2000) supra). It is contemplated that CP2 binding to TER promotes template boundary definition either via contributing to the stabilization of the RNP complex or, like the TRBD, it may act as an anchor that prevents slippage of the active site of the RT domain beyond the RNA template.

EXAMPLE 2

Efficacy of Telomerase Inhibitors

Novel telomerase inhibitors of the instant invention can be analyzed in a variety of systems. The compounds can be assessed in defined well-known model systems used to assess cellular permeability, toxicity, and pharmacodynamic effects. These assays include both cell-based and animal based assays.

Cell-Based Assay. Cells from a P388 cell line (CellGate, Inc., Sunnyvale, Calif.) or human malignant melanoma cell line SK-MEL-2 are grown in RPMI 1640 cell medium containing fetal calf serum (10%), L-glutamine, penicillin, streptomycin and are split twice weekly. All compounds are first diluted with DMSO. Later serial dilutions are done with a phosphate-buffered saline solution. All dilutions are done in glass vials and the final DMSO concentration is generally below 0.5% by volume. Final two-fold dilutions are done in a 96-well plate using cell media so that each well contains 50 µL. All compounds are assayed over multiple concentrations. Cell concentration is measured using a hemacytometer and the final cell concentration is adjusted to about $1 \times 10^4$ cells/mL with cell medium. The resulting solution of cells (50 µL) is then added to each well and the plates are incubated for 5 days in a 37° C., 5% $CO_2$, humidified incubator. MTT solution (3-[4,5-dimethylthiazol-2-yl]-2,5-diphenyltetrazolium bromide, 10 µL) is then added to each well and the plates are re-incubated under identical conditions for 2 hours. To each well is then added acidified isopropanol (150 µL of i-PrOH solution containing 0.05 N HCl) and mixed thoroughly. The plates are then scanned at 595 nm and the absorbances are read (Wallac Victor 1420 Multilabel Counter). The resulting data is then analyzed to determine an $ED_{50}$ value. Compounds that kill cancer cells, but fail to kill normal cells, find application in the prevention or treatment of cancer.

Mouse Ovarian Carcinoma Zenograft Model. Compounds of the invention are evaluated in an ovarian carcinoma xenograft model of cancer, based on that described by Davis, et al. ((1993) Cancer Research 53:2087-2091). This model, in brief, involves inoculating female nu/nu mice with $1 \times 10^9$ OVCAR3-icr cells into the peritoneal cavity. One or more test compounds are administered, e.g., prior to or after tumor cell injection, by the oral route as a suspension in 1% methyl cellulose or intraperitoneally as a suspension in phosphate-buffered saline in 0.01% TWEEN-20. At the conclusion of the experiment (4-5 weeks) the number of peritoneal cells are counted and any solid tumor deposits weighed. In some experiments tumor development is monitored by measurement of tumor specific antigens.

Rat Mammary Carcinoma Model. Compounds of the invention are evaluated in a HOSP.1 rat mammary carcinoma model of cancer (Eccles, et al. (1995) *Cancer Res.* 56:2815-2822). This model involves the intravenous inoculation of $2 \times 10^4$ tumor cells into the jugular vein of female CBH/cbi rats. One or more test compounds are administered, e.g., prior to or after tumor cell injection, by the oral route as a suspension in 1% methyl cellulose or intraperitoneally as a suspension in phosphate-buffered saline and 0.01% TWEEN-20. At the conclusion of the experiment (4-5 weeks) the animals are killed, the lungs are removed and individual tumors counted after 20 hours fixation in Methacarn.

Mouse B16 Melanoma Model. The anti-metastatic potential of compounds of the invention is evaluated in a B16 melanoma model in C57BL/6. Mice are injected intravenously with $2 \times 10^5$ B16/F10 murine tumor cells harvested from in vitro cultures. Inhibitors are administered by the oral route as a suspension in 1% methyl cellulose or intraperitoneally as a suspension in phosphate-buffered saline pH 7.2 and 0.01% TWEEN-20. Mice are killed 14 days after cell inoculation and the lungs removed and weighed prior to fixing in Bouin's solution. The number of colonies present on the surface of each set of lungs is then counted.

---

What is claimed is:

1. A pharmaceutical composition comprising 5-{[(4-methoxyphenyl)acetyl]amino}isophthalic acid and one or more cancer chemotherapeutic agents or antiproliferative agents in admixture with a pharmaceutically acceptable carrier.

* * * * *

SEQUENCE LISTING

```
<160> NUMBER OF SEQ ID NOS: 8

<210> SEQ ID NO 1
<211> LENGTH: 282
<212> TYPE: PRT
<213> ORGANISM: Tetrahymena thermophila

<400> SEQUENCE: 1

Ser Ser Phe Phe Asn Tyr Ser Glu Ile Lys Lys Gly Phe Gln Phe Lys
1               5                   10                  15

Val Ile Gln Glu Lys Leu Gln Gly Arg Gln Phe Ile Asn Ser Asp Lys
            20                  25                  30

Ile Lys Pro Asp His Pro Gln Thr Ile Ile Lys Lys Thr Leu Leu Lys
        35                  40                  45

Glu Tyr Gln Ser Lys Asn Phe Ser Cys Gln Glu Glu Arg Asp Leu Phe
    50                  55                  60

Leu Glu Phe Thr Glu Lys Ile Val Gln Asn Phe His Asn Ile Asn Phe
65                  70                  75                  80

Asn Tyr Leu Leu Lys Lys Phe Cys Lys Leu Pro Glu Asn Tyr Gln Ser
                85                  90                  95

Leu Lys Ser Gln Val Lys Gln Ile Val Gln Ser Glu Asn Lys Ala Asn
            100                 105                 110
```

```
Gln Gln Ser Cys Glu Asn Leu Phe Asn Ser Leu Tyr Asp Thr Glu Ile
        115                 120                 125

Ser Tyr Lys Gln Ile Thr Asn Phe Leu Arg Gln Ile Ile Gln Asn Cys
130                 135                 140

Val Pro Asn Gln Leu Leu Gly Lys Lys Asn Phe Lys Val Phe Leu Glu
145                 150                 155                 160

Lys Leu Tyr Glu Phe Val Gln Met Lys Arg Phe Glu Asn Gln Lys Val
                165                 170                 175

Leu Asp Tyr Ile Cys Phe Met Asp Val Phe Asp Val Glu Trp Phe Val
                180                 185                 190

Asp Leu Lys Asn Gln Lys Phe Thr Gln Lys Arg Lys Tyr Ile Ser Asp
            195                 200                 205

Lys Arg Lys Ile Leu Gly Asp Leu Ile Val Phe Ile Ile Asn Lys Ile
210                 215                 220

Val Ile Pro Val Leu Arg Tyr Asn Phe Tyr Ile Thr Glu Lys His Lys
225                 230                 235                 240

Glu Gly Ser Gln Ile Phe Tyr Tyr Arg Lys Pro Ile Trp Lys Leu Val
                245                 250                 255

Ser Lys Leu Thr Ile Val Lys Leu Glu Glu Glu Asn Leu Glu Lys Val
            260                 265                 270

Glu Glu Lys Leu Ile Pro Glu Asp Ser Phe
        275                 280

<210> SEQ ID NO 2
<211> LENGTH: 255
<212> TYPE: PRT
<213> ORGANISM: Euplotes aediculatus

<400> SEQUENCE: 2

Asn Gln Phe Phe Lys Lys His Glu Phe Val Ser Asn Lys Asn Asn Ile
1               5                   10                  15

Ser Ala Met Asp Arg Ala Gln Thr Ile Phe Thr Asn Ile Phe Arg Phe
            20                  25                  30

Asn Arg Ile Arg Lys Lys Leu Lys Asp Lys Val Ile Glu Lys Ile Ala
        35                  40                  45

Tyr Met Leu Glu Lys Val Lys Asp Phe Asn Phe Asn Tyr Tyr Leu Thr
50                  55                  60

Lys Ser Cys Pro Leu Pro Glu Asn Trp Arg Glu Arg Lys Gln Lys Ile
65                  70                  75                  80

Glu Asn Leu Ile Asn Lys Thr Arg Glu Glu Lys Ser Lys Tyr Tyr Glu
                85                  90                  95

Glu Leu Phe Ser Tyr Thr Thr Asp Asn Lys Cys Val Thr Gln Phe Ile
            100                 105                 110

Asn Glu Phe Phe Tyr Asn Ile Leu Pro Lys Asp Phe Leu Thr Gly Arg
        115                 120                 125

Asn Arg Lys Asn Phe Gln Lys Lys Val Lys Lys Tyr Val Glu Leu Asn
    130                 135                 140

Lys His Glu Leu Ile His Lys Asn Leu Leu Glu Lys Ile Asn Thr
145                 150                 155                 160

Arg Glu Ile Ser Trp Met Gln Val Glu Thr Ser Ala Lys His Phe Tyr
                165                 170                 175

Tyr Phe Asp His Glu Asn Ile Tyr Val Leu Trp Lys Leu Leu Arg Trp
            180                 185                 190

Ile Phe Glu Asp Leu Val Val Ser Leu Ile Arg Cys Phe Phe Tyr Val
        195                 200                 205
```

```
Thr Glu Gln Gln Lys Ser Tyr Ser Lys Thr Tyr Tyr Arg Lys Asn
    210                 215                 220

Ile Trp Asp Val Ile Met Lys Met Ser Ile Ala Asp Leu Lys Lys Glu
225                 230                 235                 240

Thr Leu Ala Glu Val Gln Glu Lys Val Glu Glu Trp Lys Lys
                245                 250                 255

<210> SEQ ID NO 3
<211> LENGTH: 251
<212> TYPE: PRT
<213> ORGANISM: Oxytricha trifallax

<400> SEQUENCE: 3

Phe Phe Gln Lys His Ile Leu Asn Ser Lys Thr Leu Ser Gln Gln Gln
1               5                   10                  15

Ile Arg Asp Asn Ile Tyr Lys Glu Val Phe Gly Phe Asn Arg Val Arg
                20                  25                  30

Ala Glu Leu Lys Gly Lys Val Met Ser Ile Ile Glu Gln Val Ile Val
            35                  40                  45

Asn Gln Lys Lys Phe Asp Phe Lys Tyr Tyr Leu Ser Lys Asn Cys Pro
50                  55                  60

Leu Pro Glu Asn Trp Lys Asn Leu Lys Lys Ser Phe Leu Glu Asp Ala
65                  70                  75                  80

Ala Val Ser Gly Glu Leu Arg Gly Gln Val Phe Arg Gln Leu Phe Glu
                85                  90                  95

Tyr Gln Gln Asp Gln Arg Gln Ile Ser Asn Phe Leu Thr Glu Phe Val
            100                 105                 110

Ala Asn Val Phe Pro Lys Asn Phe Leu Glu Gly Lys Asn Lys Lys Ile
        115                 120                 125

Phe Asn Lys Lys Met Leu Gln Phe Val Lys Phe Asn Arg Phe Glu Ser
130                 135                 140

Phe Thr Lys Ile Ser Leu Leu Asn Lys Phe Arg Val Asn Glu Val Ser
145                 150                 155                 160

Trp Leu Ser Phe Lys Cys Lys Asp Glu Asn Lys Lys Phe Phe Met Asn
                165                 170                 175

Glu Asn Glu His Val Phe Phe Lys Val Leu Lys Trp Val Phe Glu Asp
            180                 185                 190

Leu Ala Ile Thr Leu Met Arg Cys Tyr Phe Tyr Ser Thr Glu Lys Ala
        195                 200                 205

Lys Glu Tyr Gln Arg Ile Phe Tyr Tyr Arg Lys Asn Ile Trp Asn Met
    210                 215                 220

Ile Met Arg Leu Ser Ile Asp Asp Leu Leu Lys Gln Asn Leu Lys Gln
225                 230                 235                 240

Val Gln Glu Lys Glu Val Glu Trp Lys Lys
                245                 250

<210> SEQ ID NO 4
<211> LENGTH: 296
<212> TYPE: PRT
<213> ORGANISM: Homo sapiens

<400> SEQUENCE: 4

Pro Trp Asp Thr Pro Cys Pro Pro Val Tyr Ala Glu Thr Lys His Phe
1               5                   10                  15

Leu Tyr Ser Ser Gly Asp Lys Glu Gln Leu Arg Pro Ser Phe Leu Leu
                20                  25                  30

Ser Ser Leu Arg Pro Ser Leu Thr Gly Ala Arg Arg Leu Val Glu Thr
```

```
                     35                  40                  45
Ile Phe Leu Gly Ser Arg Pro Trp Met Pro Gly Thr Pro Arg Arg Leu
 50                  55                  60

Pro Arg Leu Pro Gln Arg Tyr Trp Gln Met Arg Pro Leu Phe Leu Glu
 65                  70                  75                  80

Leu Leu Gly Asn His Ala Gln Cys Pro Tyr Gly Val Leu Leu Lys Thr
                     85                  90                  95

His Cys Pro Leu Arg Ala Ala Val Thr Pro Ala Ala Gly Val Cys Ala
                100                 105                 110

Arg Glu Lys Pro Gln Gly Ser Val Ala Ala Pro Glu Glu Glu Asp Thr
            115                 120                 125

Asp Pro Arg Arg Leu Val Gln Leu Leu Arg Gln His Ser Ser Pro Trp
130                 135                 140

Gln Val Tyr Gly Phe Val Arg Ala Cys Leu Arg Arg Leu Val Pro Pro
145                 150                 155                 160

Gly Leu Trp Gly Ser Arg His Asn Glu Arg Arg Phe Leu Arg Asn Thr
                165                 170                 175

Lys Lys Phe Ile Ser Leu Gly Lys His Ala Lys Leu Ser Leu Gln Glu
            180                 185                 190

Leu Thr Trp Lys Met Ser Val Arg Asp Cys Ala Trp Leu Arg Arg Ser
        195                 200                 205

Pro Gly Val Gly Cys Val Pro Ala Ala Glu His Arg Leu Arg Glu Glu
210                 215                 220

Ile Leu Ala Lys Phe Leu His Trp Leu Met Ser Val Tyr Val Val Glu
225                 230                 235                 240

Leu Leu Arg Ser Phe Phe Tyr Val Thr Glu Thr Thr Phe Gln Lys Asn
                245                 250                 255

Arg Leu Phe Phe Tyr Arg Lys Ser Val Trp Ser Lys Leu Gln Ser Ile
            260                 265                 270

Gly Ile Arg Gln His Leu Lys Arg Val Gln Leu Arg Glu Leu Ser Glu
        275                 280                 285

Ala Glu Val Arg Gln His Arg Glu
    290                 295

<210> SEQ ID NO 5
<211> LENGTH: 281
<212> TYPE: PRT
<213> ORGANISM: Mus musculus

<400> SEQUENCE: 5

Gln Asn Ala Phe Gln Leu Arg Pro Phe Ile Glu Thr Arg His Phe Leu
 1               5                  10                  15

Tyr Ser Arg Gly Asp Gly Gln Glu Arg Leu Asn Pro Ser Phe Leu Leu
             20                  25                  30

Ser Asn Leu Gln Pro Asn Leu Thr Gly Ala Arg Arg Leu Val Glu Ile
         35                  40                  45

Ile Phe Leu Gly Ser Arg Pro Arg Thr Ser Gly Pro Leu Cys Arg Thr
 50                  55                  60

His Arg Leu Ser Arg Arg Tyr Trp Gln Met Arg Pro Leu Phe Gln Gln
 65                  70                  75                  80

Leu Leu Val Asn His Ala Glu Cys Gln Tyr Val Arg Leu Leu Arg Ser
                 85                  90                  95

His Cys Arg Phe Arg Thr Ala Asn Gln Gln Val Thr Asp Ala Leu Asn
                100                 105                 110

Thr Ser Pro Pro His Leu Met Asp Leu Leu Arg Leu His Ser Ser Pro
```

```
            115                 120                 125
Trp Gln Val Tyr Gly Phe Leu Arg Ala Cys Leu Cys Lys Val Val Ser
130                 135                 140

Ala Ser Leu Trp Gly Thr Arg His Asn Glu Arg Arg Phe Phe Lys Asn
145                 150                 155                 160

Leu Lys Lys Phe Ile Ser Leu Gly Lys Tyr Gly Lys Leu Ser Leu Gln
                165                 170                 175

Glu Leu Met Trp Lys Met Lys Val Glu Asp Cys His Trp Leu Arg Ser
            180                 185                 190

Ser Pro Gly Lys Asp Arg Val Pro Ala Ala Glu His Arg Leu Arg Glu
        195                 200                 205

Arg Ile Leu Ala Thr Phe Leu Phe Trp Leu Met Asp Thr Tyr Val Val
    210                 215                 220

Gln Leu Leu Arg Ser Phe Phe Tyr Ile Thr Glu Ser Thr Phe Gln Lys
225                 230                 235                 240

Asn Arg Leu Phe Phe Tyr Arg Lys Ser Val Trp Ser Lys Leu Gln Ser
                245                 250                 255

Ile Gly Val Arg Gln His Leu Glu Arg Val Arg Leu Arg Glu Leu Ser
            260                 265                 270

Gln Glu Glu Val Arg His His Gln Asp
        275                 280

<210> SEQ ID NO 6
<211> LENGTH: 234
<212> TYPE: PRT
<213> ORGANISM: Schizosaccharomyces pombe

<400> SEQUENCE: 6

Gln Trp Ile Phe Pro Arg Gln Phe Gly Leu Ile Asn Ala Phe Gln Val
1               5                   10                  15

Lys Gln Leu His Lys Val Ile Pro Leu Val Ser Gln Ser Thr Val Val
            20                  25                  30

Pro Lys Arg Leu Leu Lys Val Tyr Pro Leu Ile Glu Gln Thr Ala Lys
        35                  40                  45

Arg Leu His Arg Ile Ser Leu Ser Lys Val Tyr Asn His Tyr Cys Pro
    50                  55                  60

Tyr Ile Asp Thr His Asp Asp Glu Lys Ile Leu Ser Tyr Ser Leu Lys
65                  70                  75                  80

Pro Asn Gln Val Phe Ala Phe Leu Arg Ser Ile Leu Val Arg Val Phe
                85                  90                  95

Pro Lys Leu Ile Trp Gly Asn Gln Arg Ile Phe Glu Ile Ile Leu Lys
            100                 105                 110

Asp Leu Glu Thr Phe Leu Lys Leu Ser Arg Tyr Glu Ser Phe Ser Leu
        115                 120                 125

His Tyr Leu Met Ser Asn Ile Lys Ile Ser Glu Ile Glu Trp Leu Val
    130                 135                 140

Leu Gly Lys Arg Ser Asn Ala Lys Met Cys Leu Ser Asp Phe Glu Lys
145                 150                 155                 160

Arg Lys Gln Ile Phe Ala Glu Phe Ile Tyr Trp Leu Tyr Asn Ser Phe
                165                 170                 175

Ile Ile Pro Ile Leu Gln Ser Phe Phe Tyr Ile Thr Glu Ser Ser Asp
            180                 185                 190

Leu Arg Asn Arg Thr Val Tyr Phe Arg Lys Asp Ile Trp Lys Leu Leu
        195                 200                 205

Cys Arg Pro Phe Ile Thr Ser Met Lys Met Glu Ala Phe Glu Lys Ile
```

```
                210                 215                 220
Asn Glu Asn Asn Val Arg Met Asp Thr Gln
225                 230
```

<210> SEQ ID NO 7
<211> LENGTH: 232
<212> TYPE: PRT
<213> ORGANISM: Saccharomyces cerevisiae

<400> SEQUENCE: 7

```
Ser Ser Phe Phe Pro Tyr Ser Lys Ile Leu Pro Ser Ser Ser Ser Ile
1               5                   10                  15

Lys Lys Leu Thr Asp Leu Arg Glu Ala Ile Phe Pro Thr Asn Leu Val
            20                  25                  30

Lys Ile Pro Gln Arg Leu Lys Val Arg Ile Asn Leu Thr Leu Gln Lys
        35                  40                  45

Leu Leu Lys Arg His Lys Arg Leu Asn Tyr Val Ser Ile Leu Asn Ser
    50                  55                  60

Ile Cys Pro Pro Leu Glu Gly Thr Val Leu Asp Leu Ser His Leu Ser
65                  70                  75                  80

Arg Gln Ser Pro Lys Glu Arg Val Leu Lys Phe Ile Val Ile Leu
                85                  90                  95

Gln Lys Leu Leu Pro Gln Glu Met Phe Gly Ser Lys Lys Asn Lys Gly
            100                 105                 110

Lys Ile Ile Lys Asn Leu Asn Leu Leu Ser Leu Pro Leu Asn Gly
        115                 120                 125

Tyr Leu Pro Phe Asp Ser Leu Leu Lys Lys Leu Arg Leu Lys Asp Phe
    130                 135                 140

Arg Trp Leu Phe Ile Ser Asp Ile Trp Phe Thr Lys His Asn Phe Glu
145                 150                 155                 160

Asn Leu Asn Gln Leu Ala Ile Cys Phe Ile Ser Trp Leu Phe Arg Gln
                165                 170                 175

Leu Ile Pro Lys Ile Ile Gln Thr Phe Phe Tyr Cys Thr Glu Ile Ser
            180                 185                 190

Ser Thr Val Thr Ile Val Tyr Phe Arg His Asp Thr Trp Asn Lys Leu
        195                 200                 205

Ile Thr Pro Phe Ile Val Glu Tyr Phe Lys Thr Tyr Leu Val Glu Asn
    210                 215                 220

Asn Val Cys Arg Asn His Asn Ser
225                 230
```

<210> SEQ ID NO 8
<211> LENGTH: 313
<212> TYPE: PRT
<213> ORGANISM: Arabidopsis thaliana

<400> SEQUENCE: 8

```
Thr Asp Phe Val Lys Gln Ala Lys Gln Val Lys Arg Asn Lys Asn Phe
1               5                   10                  15

Lys Phe Gly Leu Ser Glu Thr Tyr Ser Val Ile Pro Pro Asn His Ile
            20                  25                  30

Leu Lys Thr Leu Arg Pro Asn Cys Ser Asp Ser Lys Leu Leu Met Asn
        35                  40                  45

His Ile Phe Gly Glu Val Asn Val Trp Ser Thr Thr Pro Ser His Gly
    50                  55                  60

Lys Gly Asn Cys Pro Ser Gly Ser Ile Cys Leu Tyr His Ser Leu Leu
65                  70                  75                  80
```

```
Lys Ser Leu Lys Asn Leu Ile Gly Lys Thr Lys Ser Ser His Leu Lys
                85              90              95

Met Leu Leu Asp Lys His Cys Pro Val Leu Leu Leu Gln Glu Asp Ala
            100             105             110

Leu Lys Ser Gly Thr Thr Ser Gln Ser Ser Arg Arg Gln Lys Ala Asp
        115             120             125

Lys Leu Pro His Gly Ser Ser Ser Ser Gln Thr Gly Lys Pro Lys Cys
    130             135             140

Pro Ser Val Glu Glu Arg Lys Leu Tyr Cys Thr Asn Asp Gln Val Val
145             150             155             160

Ser Phe Ile Trp Ala Ile Cys Arg Tyr Ile Val Pro Glu Ser Leu Leu
                165             170             175

Gly Thr Thr His Gln Met Arg Val Leu Arg Lys Asn Ile Ala Trp Phe
            180             185             190

Val Ser Arg Arg Arg Asn Glu Lys Cys Thr Val Asn Gln Phe Leu His
        195             200             205

Lys Val Lys Pro Ser Asp Phe Pro Phe Ala Arg Lys Glu Leu Cys
    210             215             220

Cys Met Val Asn Gly His Glu Leu Gln Ser Glu Ser Ile Arg Ser Thr
225             230             235             240

Gln Gln Met Leu Cys Thr Lys Trp Ile Ser Trp Leu Phe Leu Glu Ile
                245             250             255

Val Lys Lys Leu Val His Phe Asn Phe Tyr Ala Thr Glu Ser Gln Gly
            260             265             270

Gly Arg Leu Asn Ile Tyr Tyr Tyr Arg Lys Arg Ser Trp Glu Arg Leu
        275             280             285

Ile Ser Lys Glu Ile Ser Lys Ala Leu Asp Gly Tyr Val Leu Val Asp
    290             295             300

Asp Ala Glu Ala Glu Ser Ser Arg Lys
305             310
```